(12) United States Patent
Wallach et al.

(10) Patent No.: US 8,362,206 B2
(45) Date of Patent: Jan. 29, 2013

(54) CHIMERIC PROTEINS AND USES THEREOF

(75) Inventors: David Wallach, Rehovot (IL); Elena Appel, Rishon Le Zion (IL); Tanya Goncahrov, Ashkelon (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 815 days.

(21) Appl. No.: 11/629,258

(22) PCT Filed: Jun. 28, 2005

(86) PCT No.: PCT/IL2005/000689
§ 371 (c)(1),
(2), (4) Date: Jul. 30, 2008

(87) PCT Pub. No.: WO2006/001023
PCT Pub. Date: Jan. 5, 2006

(65) Prior Publication Data
US 2011/0123480 A1 May 26, 2011

Related U.S. Application Data

(60) Provisional application No. 60/582,827, filed on Jun. 28, 2004.

(51) Int. Cl.
C07K 14/715 (2006.01)
C07K 19/00 (2006.01)
C12N 15/62 (2006.01)
C12N 15/63 (2006.01)
C12N 15/79 (2006.01)
C12N 15/85 (2006.01)
C12N 15/81 (2006.01)
A61K 38/16 (2006.01)
A61K 35/74 (2006.01)

(52) U.S. Cl. ............ 530/350; 530/825; 424/236.1; 424/260.1; 536/23.4; 514/1.1; 435/320.1; 435/367; 435/358; 435/369; 435/372; 435/254.2; 435/348; 435/252.3; 435/69.7

(58) Field of Classification Search .................. None
See application file for complete search history.

(56) References Cited

U.S. PATENT DOCUMENTS

| 5,510,256 A | * | 4/1996 | Kirschner et al. | 435/91.41 |
| 5,656,272 A | * | 8/1997 | Le et al. | 424/133.1 |
| 6,881,718 B1 | * | 4/2005 | FitzGerald et al. | 514/2.4 |
| 7,238,776 B2 | * | 7/2007 | Hauptmann et al. | 530/350 |
| 2004/0009552 A1 | | 1/2004 | Adams et al. | |
| 2004/0018203 A1 | * | 1/2004 | Pastan et al. | 424/178.1 |

FOREIGN PATENT DOCUMENTS

| EP | 0 383 599 | 8/1990 |
| WO | WO 99/10484 | 3/1999 |
| WO | WO 00/40716 | 7/2000 |

OTHER PUBLICATIONS

Scallon et al. Chimeric anti-TNF-alpha monoclonal antibody cA2 binds recombinant transmembrane TNF-alpha and activates immune effector functions. Cytokine. Apr. 1997;7(3):251-9.*
Shurety et al. Endocytosis of uncleaved tumor necrosis factor-alpha in macrophages. Lab Invest. Jan. 2001;81(1):107-17.*
Yu et al. Circular permutation: a different way to engineer enzyme structure and function. Trends Biotechnol. Jan. 2011;29(1):18-25. Epub Nov. 17, 2010.*
Bowie et al. Deciphering the message in protein sequences: tolerance to amino acid substitutions. Science, (Mar. 16, 1990) 247 (4948) 1306-10.*
Ngo et al., in the Protein Folding Problem and Tertiary Structure Prediction, Merz and Le Grand (Eds), Aug. 1994, Springer Verlag, pp. 433 and 492-495.*
Guo et al. Protein tolerance to random amino acid change. Proc Natl Acad Sci U S A. Jun. 22, 2004;101(25):9205-10.*
Chaudhary et al. Selective killing of HIV-infected cells by recombinant human CD4-Pseudomonas exotoxin hybrid protein. Nature. Sep. 22, 1988;335(6188):369-72.*
Andreakos, Cytokines and anti-cytokine biologicals in autoimmunity: present and future, Cytokine Growth Factor Rev., 13:299-313, 2002.
Ben-Yehudah et al., Utilizing chimeric proteins for exploring the cellular fate of endogenous proteins, Biochem. Biophys. Res. Commun., 290:332-338, 2002.
Berger et al., CD-4 Pseudomonas exotoxin hybrid protein blocks the spread of human immunodeficiency virus infection in vitro and is active against cells expressing the envelope glycoproteins from diverse primate immunodeficiency viruses, Proc. Natl. Acad. Sci. USA, 86:9539-9543, 1989.
Beulter, The role of tumor necrosis factor in health and disease, J. Rheumatol., 26(suppl. 57):18-21, 1999.
Bigda et al., Dual role of the p75 tumor necrosis factor (TNF) receptor in TNF cytotoxicity, J. Exp. Med., 180:445-460, 1994.
Brinkmann et al., Recombinant immunotoxins, From Basic Res. to Cancer Ther. Met., 8:143-156, 1995.
Engelmann et al., Antibodies to a soluble form of a tumors necrosis factor (TNF) receptor have TNF-like activity, J. Biol. Chem., 265:14497-14504, 1990.
Feldmann et al., Anti TNF alpha therapy of rheumatoid arthritis: what have we learned?, Ann. Rev. Immunol., 19:163-196, 2001.
International Search Report, PCT/IL2005/000689, European Patent Office, mailed Dec. 20, 2005.
Jankovic et al., Th2-cell commitment during infectious disease: asymmetry of divergent pathways, Trends Immunol., 22:450-457, 2001.
Keffer et al., Transgenic mice expressing human tumour necrosis factor: a predictive genetic model of arthritis, EMBO J., 10:4025-4031, 1991.
Kollias et al., The role of tumor necrosis factor and receptors in models of multiorgan failure, rheumatoid arthritis, multiple sclerosis, and inflammatory bowel disease, Immunol. Rev., 169:175-194, 1999.
Kreitman, Immunotoxins containing Pseudomonas exotoxin A: a short history, Cancer Immunol. Immunother., 52:338-341, 2003.

(Continued)

Primary Examiner — David Romeo
(74) Attorney, Agent, or Firm — Marshall, Gerstein & Borun LLP

(57) ABSTRACT

The present invention provides a chimeric protein capable of killing or modifying a cell expressing abnormally high levels of a ligand of a receptor of the TNF/NGF family, comprising the amino acid sequence of at least one polypeptide consisting of an extracellular portion of said receptor connected to an effector molecule. In addition the invention provides pharmaceutical compositions comprising said chimeric protein and use thereof.

17 Claims, 10 Drawing Sheets

OTHER PUBLICATIONS

Kunzendorf et al., Immunomodulation in experimental and clinical nephrology using chimeric proteins, Kidney and Blood Pressure Res., 19:201-204, 1996.

Locksley et al., TNF and TNF receptor superfamilies: integrating mammalian biology, Cell, 104:487-501, 2001.

Lugering et al., Infliximab induces apoptosis in monocytes from patients with chronic active Crohn's disease by using a caspase-dependent pathway, Gastroenterology, 121:1145-1157, 2001.

Pastan et al., Immunotoxins for targeted cancer therapy, Adv. Drug Deliv. Rev., 31:53-88, 1998.

Reimold, New indications for treatment of chronic inflammation by TNF-alpha blockade, Am. J. Med. Sci., 325:75-92, 2003.

Scheinin et al., Validation of the interleukin-10 knockout mouse model of colitis: antitumour necrosis factor-antibodies suppress the progression of colitis, Clinicia Exp. Immu., 133:38-43, 2003.

Van Den Brande et al., Infliximab but not etanercept induces apoptosis in lamina propria T-lymphocytes from patients with Crohn's disease, Gastroenterology, 124:1774-1785, 2003.

Van Deventer, Transmembrane TNF-alpha, induction of apoptosis, and the efficacy of TNF-targeting therapies in Crohn's disease, Gastroenterology, 121:1242-1246, 2001.

Wallach et al., Tumor necrosis factor receptor and Fas signaling mechanisms, Ann. Rev. Immunol., 17:331-167, 1999.

Written Opinion of the International Searching Authority, PCT/IL2005/000689, European Patent Office, mailed Dec. 20, 2005.

\* cited by examiner

TBPI — Pseudomonas exotoxin II-III

Fig. 1A

Furine cleavage site
↓

Cell binding domain   Translocating domain   ADP-ribosylating domain

Fig. 1B

```
gatagtgtgtgtccccaaggaaaatatatccaccctcaaaataattcgatttgctgtacc
aagtgccacaaaggaacctacttgtacaatgactgtccaggcccggggcaggatacggac
tgcagggagtgtgagagcggctccttcaccgcttcagaaaaccacctcagacactgcctc
agctgctccaaatgccgaaaggaaatgggtcaggtggagatctcttcttgcacagtggac
cgggacaccgtgtgtggctgcaggaagaaccagtaccggcattattggagtgaaaacctt
ttccagtgcttcaattgcagcctctgcctcaatgggaccgtgcacctctcctgccaggag
aaacagaacaccgtgtgcacctgccatgcaggtttctttctaagagaaaacgagtgtgtc
tcctgtagtaactgtaagaaaagcctggagtgcacgaagttgtgcctaccccagattgag
aataaagcttccggaggtcccgagggcggcagcctggccgcgctgaccgcgcaccaggct
tgccacctgccgctggagactttcacccgtcatcgccagccgcgcggctgggaacaactg
gagcagtgcggctatccggtgcagcggctggtcgccctctacctggcggcgcggctgtcg
tggaaccaggtcgaccaggtgatccgcaacgccctggccagccccggcagcggcggcgac
ctgggcgaagcgatccgcgagcagccggagcaggcccgtctggccctgaccctggccgcc
gccgagagcgagcgcttcgtccggcagggcaccggcaacgacgaggccggcgcggccaac
gccgacgtggtgagcctgacctgcccggtcgccgccggtgaatgcgcgggcccggcggac
agcggcgacgccctgctggagcgcaactatcccactggcgcggagttcctcggcgacggc
ggcgacgtcagcttcagcacccgcggcacgcagaactggacggtggagcggctgctccag
gcgcaccgccaactggaggagcgcggctatgtgttcgtcggctaccacggcaccttcctc
gaagcggcgcaaagcatcgtcttcggcggggtgcgcgcgcgcagccaggacctcgacgcg
atctggcgcggtttctatatcgccggcgatccggcgctggcctacggctacgcccaggac
caggaacccgacgcacgcggccggatccgcaacggtgccctgctgcgggtctatgtgccg
cgctcgagcctgccgggcttctaccgcaccagcctgaccctggccgcgccggaggcggcg
ggcgaggtcgaacggctgatcggccatccgctgccgctgcgcctggacgccatcaccggc
cccgaggaggaaggcgggcgcctggagaccattctcggctggccgctggccgagcgcacc
gtggtgattccctcggcgatccccaccgaccgcgcaacgtcggcggcgacctcgacccg
tccagcatccccgacaaggaacaggcgatcagcgccctgccggactacgccagccagccc
ggcaaaccgccgcgcgaggacctgaag
```

Fig. 1C

*DSVCPQGKYIHPQNNSICCTKCHKGTYLYNDCPGPGQDTDCRECESGSFTASENHLR*
*HCLSCSKCRKEMGQVEISSCTVDRDTVCGCRKNQYRHYWSENLFQCFNCSLCLNGTV*
*HLSCQEKQNTVCTCHAGFFLRENECVSCSNCKKSLECTKLCLPQIE*NASGGPEGGSL
AALTAHQACHLPLETFTRHRQPRGWEQLEQCGYPVQRLVALYLAARLSWNQV
DQVIRNALASPGSGGDLGEAIREQPEQARLALTLAAAESERFVRQGTGNDEAGA
ANADVVSLTCPVAAGECAGPADSGDALLERNYPTGAEFLGDGGDVSFSTRGTQ
NWTVERLLQAHRQLEERGYVFVGYHGTFLEAAQSIVFGGVRARSQDLDAIWRG
FYIAGDPALAYGYAQDQEPDARGRIRNGALLRVYVPRSSLPGFYRTSLTLAAPEA
AGEVERLIGHPLPLRLDAITGPEEEGGRLETILGWPLAERTVVIPSAIP*TDPRNVGG*
*DLDPSSIPDKEQAISALPDYASQPGKPPREDLK*

Fig. 1D

```
ggcggcagcctggccgcgctgaccgcgcaccaggcttgccacctgccgctggagactttc
acccgtcatcgccagccgcgcggctgggaacaactggagcagtgcggctatccggtgcag
cggctggtcgccctctacctggcggcgcggctgtcgtggaaccaggtcgaccaggtgatc
cgcaacgccctggccagccccggcagcggcggcgacctgggcgaagcgatccgcgagcag
ccggagcaggcccgtctggccctgaccctggccgccgccgagagcgagcgcttcgtccgg
cagggcaccggcaacgacgaggccggcgcggccaacgccgacgtggtgagcctgacctgc
ccggtcgccgccggtgaatgcgcgggcccggcggacagcggcgacgccctgctggagcgc
aactatcccactggcgcggagttcctcggcgacggcggcgacgtcagcttcagcacccgc
ggcacgcagaactggacggtggagcggctgctccaggcgcaccgccaactggaggagcgc
ggctatgtgttcgtcggctaccacggcaccttcctcgaagcggcgcaaagcatcgtcttc
ggcggggtgcgcgcgcgcagccaggacctcgacgcgatctggcgcggtttctatatcgcc
ggcgatccggcgctggcctacggctacgcccaggaccaggaacccgacgcacgcggccgg
atccgcaacggtgccctgctgcgggtctatgtgccgcgctcgagcctgccgggcttctac
cgcaccagcctgaccctggccgcgccggaggcggcgggcgaggtcgaacggctgatcggc
catccgctgccgctgcgcctggacgccatcaccggccccgaggaggaaggcgggcgcctg
gagaccattctcggctggccgctggccgagcgcaccgtggtgattccctcggcgatcccc
accgaccgcgcaacgtcggcggcgacctcgaccgtccagcatccccgacaaggaacag
gcgatcagcgccctgccggactacgccagccagcccggcaaaccgccgcgcgaggacctg
aag
```

Fig. 1E

GGSLAALTAHQACHLPLETFTRHRQPRGWEQLEQCGYPVQRLVALYLAARLSW
NQVDQVIRNALASPGSGGDLGEAIREQPEQARLALTLAAAESERFVRQGTGNDE
AGAANADVVSLTCPVAAGECAGPADSGDALLERNYPTGAEFLGDGGDVSFSTRG
TQNWTVERLLQAHRQLEERGYVFVGYHGTFLEAAQSIVFGGVRARSQDLDAIWR
GFYIAGDPALAYGYAQDQEPDARGRIRNGALLRVYVPRSSLPGFYRTSLTLAAPE
AAGEVERLIGHPLPLRLDAITGPEEEGGRLETILGWPLAERTVVIPSAIPTDPRNVG
GDLDPSSIPDKEQAISALPDYASQPGKPPREDLK

Fig. 1F aaagcttccggaggtcccgag

Fig. 1G

KASGGPE

Fig. 1H concentration of recombinant protein, ng/ml

SEQUENCE LISTING

<160> NUMBER OF SEQ ID NOS: 10

<210> SEQ ID NO 1
<211> LENGTH: 1587
<212> TYPE: DNA
<213> ORGANISM: Artificial Sequence
<220> FEATURE:
<223> OTHER INFORMATION: Chimera

<400> SEQUENCE: 1

```
gatagtgtgt gtccccaagg aaaatatatc caccctcaaa ataattcgat ttgctgtacc      60
aagtgccaca aaggaaccta cttgtacaat gactgtccag gcccggggca ggatacggac     120
tgcagggagt gtgagagcgg ctccttcacc gcttcagaaa accacctcag acactgcctc     180
agctgctcca aatgccgaaa ggaaatgggt caggtggaga tctcttcttg cacagtggac     240
cgggacaccg tgtgtggctg caggaagaac cagtaccggc attattggag tgaaaacctt     300
ttccagtgct tcaattgcag cctctgcctc aatgggaccg tgcacctctc ctgccaggag     360
aaacagaaca ccgtgtgcac ctgccatgca ggtttctttc taagagaaaa cgagtgtgtc     420
tcctgtagta actgtaagaa aagcctggag tgcacgaagt tgtgcctacc ccagattgag     480
aataaagctt ccggaggtcc cgaggcggc agcctggccg cgctgaccgc gcaccaggct     540
tgccacctgc cgctggagac tttcacccgt catcgccagc gcgcggctg gaacaactg     600 gagcagtgcg gctatccggt gcagcggctg gtcgccctct acctggcggc gcggctgtcg     660
tggaaccagg tcgaccaggt gatccgcaac gccctggcca gcccggcag cggcggcgac     720
```

```
ctgggcgaag cgatccgcga gcagccggag caggcccgtc tggccctgac cctggccgcc    780
gccgagagcg agcgcttcgt ccggcagggc accggcaacg acgaggccgg cgcggccaac    840
gccgacgtgg tgagcctgac ctgcccggtc gccgccggtg aatgcgcggg cccggcggac    900
agcggcgacc ccctgctgga gcgcaactat cccactggcg cggagttcct cggcgacggc    960
ggcgacgtca gcttcagcac ccgcggcacg cagaactgga cggtggagcg gctgctccag   1020
gcgcaccgcc aactggagga gcgcggctat gtgttcgtcg gctaccacgg caccttcctc   1080
gaagcggcgc aaagcatcgt cttcggcggg gtgcgcgcgc gcagccagga cctcgacgcg   1140
atctggcgcg gtttctatat cgccggcgat ccggcgctgg cctacggcta cgcccaggac   1200
caggaacccg acgcacgcgg ccggatccgc aacggtgccc tgctgcgggt ctatgtgccg   1260
cgctcgagcc tgccgggctt ctaccgcacc agcctgaccc tggccgcgcc ggaggcggcg   1320
ggcgaggtcg aacggctgat cggccatccg ctgccgctgc gcctggacgc catcaccggc   1380
cccgaggagg aaggcgggcg cctggagacc attctcggct ggccgctggc cgagcgcacc   1440
gtggtgattc cctcggcgat ccccaccgac ccgcgcaacg tcggcggcga cctcgacccg   1500
tccagcatcc ccgacaagga acaggcgatc agcgccctgc cggactacgc cagccagccc   1560
ggcaaaccgc cgcgcgagga cctgaag                                       1587
```

<210> SEQ ID NO 2
<211> LENGTH: 528
<212> TYPE: PRT
<213> ORGANISM: Artificial Sequence
<220> FEATURE:
<223> OTHER INFORMATION: Chimera

<400> SEQUENCE: 2

```
Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Ala Ser Gly Gly Pro Glu Gly Gly Ser Leu Ala Ala Leu Thr Ala
                165                 170                 175

His Gln Ala Cys His Leu Pro Leu Glu Thr Phe Thr Arg His Arg Gln
            180                 185                 190

Pro Arg Gly Trp Glu Gln Leu Glu Gln Cys Gly Tyr Pro Val Gln Arg
        195                 200                 205

Leu Val Ala Leu Tyr Leu Ala Ala Arg Leu Ser Trp Asn Gln Val Asp
```

```
                  210                 215                 220
Gln Val Ile Arg Asn Ala Leu Ala Ser Pro Gly Ser Gly Gly Asp Leu
225                 230                 235                 240

Gly Glu Ala Ile Arg Glu Gln Pro Glu Gln Ala Arg Leu Ala Leu Thr
                245                 250                 255

Leu Ala Ala Ala Glu Ser Glu Arg Phe Val Arg Gln Gly Thr Gly Asn
                    260                 265                 270

Asp Glu Ala Gly Ala Ala Asn Ala Asp Val Val Ser Leu Thr Cys Pro
                275                 280                 285

Val Ala Ala Gly Glu Cys Ala Gly Pro Ala Asp Ser Gly Asp Ala Leu
            290                 295                 300

Leu Glu Arg Asn Tyr Pro Thr Gly Ala Glu Phe Leu Gly Asp Gly Gly
305                 310                 315                 320

Asp Val Ser Phe Ser Thr Arg Gly Thr Gln Asn Trp Thr Val Glu Arg
                325                 330                 335

Leu Leu Gln Ala His Arg Gln Leu Glu Glu Arg Gly Tyr Val Phe Val
                340                 345                 350

Gly Tyr His Gly Thr Phe Leu Glu Ala Ala Gln Ser Ile Val Phe Gly
                355                 360                 365

Gly Val Arg Ala Arg Ser Gln Asp Leu Asp Ala Ile Trp Arg Gly Phe
            370                 375                 380

Tyr Ile Ala Gly Asp Pro Ala Leu Ala Tyr Gly Tyr Ala Gln Asp Gln
385                 390                 395                 400

Glu Pro Asp Ala Arg Gly Arg Ile Arg Asn Gly Ala Leu Leu Arg Val
                405                 410                 415

Tyr Val Pro Arg Ser Ser Leu Pro Gly Phe Tyr Arg Thr Ser Leu Thr
                420                 425                 430

Leu Ala Ala Pro Glu Ala Ala Gly Glu Val Glu Arg Leu Ile Gly His
            435                 440                 445

Pro Leu Pro Leu Arg Leu Asp Ala Ile Thr Gly Pro Glu Glu Glu Gly
        450                 455                 460

Gly Arg Leu Glu Thr Ile Leu Gly Trp Pro Leu Ala Glu Arg Thr Val
465                 470                 475                 480

Val Ile Pro Ser Ala Ile Pro Thr Asp Pro Arg Asn Val Gly Gly Asp
                485                 490                 495

Leu Asp Pro Ser Ser Ile Pro Asp Lys Glu Gln Ala Ile Ser Ala Leu
            500                 505                 510

Pro Asp Tyr Ala Ser Gln Pro Gly Lys Pro Pro Arg Glu Asp Leu Lys
        515                 520                 525

<210> SEQ ID NO 3
<211> LENGTH: 1083
<212> TYPE: DNA
<213> ORGANISM: Pseudomonas aeruginosa

<400> SEQUENCE: 3
ggcggcagcc tggccgcgct gaccgcgcac caggcttgcc acctgccgct ggagactttc      60
acccgtcatc gccagccgcg cggctgggaa caactggagc agtgcggcta tccggtgcag     120
cggctggtcg ccctctacct ggcggcgcgg ctgtcgtgga accaggtcga ccaggtgatc     180
cgcaacgccc tggccagccc cggcagcggc ggcgacctgg gcgaagcgat ccgcgagcag     240
ccggagcagg cccgtctggc cctgaccctg ccgccgccg agagcgagcg cttcgtccgg      300
cagggcaccg gcaacgacga ggccggcgcg gccaacgccg acgtggtgag cctgacctgc     360
ccggtcgccg ccggtgaatg cgcgggcccg gcggacagcg gcgacgccct gctggagcgc     420
```

```
aactatccca ctggcgcgga gttcctcggc gacggcggcg acgtcagctt cagcacccgc    480
ggcacgcaga actggacggt ggagcggctg ctccaggcgc accgccaact ggaggagcgc    540
ggctatgtgt tcgtcggcta ccacggcacc ttcctcgaag cggcgcaaag catcgtcttc    600
ggcggggtgc gcgcgcgcag ccaggacctc gacgcgatct ggcgcggttt ctatatcgcc    660
ggcgatccgg cgctggccta cggctacgcc caggaccagg aacccgacgc acgcggccgg    720
atccgcaacg gtgccctgct gcgggtctat gtgccgcgct cgagcctgcc gggcttctac    780
cgcaccagcc tgaccctggc cgcgccggag gcggcgggcg aggtcgaacg gctgatcggc    840
catccgctgc cgctgcgcct ggacgccatc accggccccg aggaggaagg cgggcgcctg    900
gagaccattc tcggctggcc gctggccgag cgcaccgtgg tgattccctc ggcgatcccc    960
accgacccgc gcaacgtcgg cggcgacctc gacccgtcca gcatccccga caaggaacag   1020
gcgatcagcg ccctgccgga ctacgccagc cagcccggca accgccgcg cgaggacctg   1080 aag                                                                 1083
```

<210> SEQ ID NO 4
<211> LENGTH: 361
<212> TYPE: PRT
<213> ORGANISM: Pseudomonas aeruginosa

<400> SEQUENCE: 4

```
Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

Ala Asp Val Val Ser Leu Thr Cys Pro Val Ala Ala Gly Glu Cys Ala
        115                 120                 125

Gly Pro Ala Asp Ser Gly Asp Ala Leu Leu Glu Arg Asn Tyr Pro Thr
    130                 135                 140

Gly Ala Glu Phe Leu Gly Asp Gly Gly Asp Val Ser Phe Ser Thr Arg
145                 150                 155                 160

Gly Thr Gln Asn Trp Thr Val Glu Arg Leu Leu Gln Ala His Arg Gln
                165                 170                 175

Leu Glu Glu Arg Gly Tyr Val Phe Val Gly Tyr His Gly Thr Phe Leu
            180                 185                 190

Glu Ala Ala Gln Ser Ile Val Phe Gly Gly Val Arg Ala Arg Ser Gln
        195                 200                 205

Asp Leu Asp Ala Ile Trp Arg Gly Phe Tyr Ile Ala Gly Asp Pro Ala
    210                 215                 220

Leu Ala Tyr Gly Tyr Ala Gln Asp Gln Glu Pro Asp Ala Arg Gly Arg
225                 230                 235                 240

Ile Arg Asn Gly Ala Leu Leu Arg Val Tyr Val Pro Arg Ser Ser Leu
                245                 250                 255
```

```
Pro Gly Phe Tyr Arg Thr Ser Leu Thr Leu Ala Ala Pro Glu Ala Ala
            260                 265                 270

Gly Glu Val Glu Arg Leu Ile Gly His Pro Leu Pro Leu Arg Leu Asp
        275                 280                 285

Ala Ile Thr Gly Pro Glu Glu Gly Gly Arg Leu Glu Thr Ile Leu
    290                 295                 300

Gly Trp Pro Leu Ala Glu Arg Thr Val Val Ile Pro Ser Ala Ile Pro
305                 310                 315                 320

Thr Asp Pro Arg Asn Val Gly Gly Asp Leu Asp Pro Ser Ser Ile Pro
                325                 330                 335

Asp Lys Glu Gln Ala Ile Ser Ala Leu Pro Asp Tyr Ala Ser Gln Pro
            340                 345                 350

Gly Lys Pro Pro Arg Glu Asp Leu Lys
        355                 360

<210> SEQ ID NO 5
<211> LENGTH: 21
<212> TYPE: DNA
<213> ORGANISM: Artificial Sequence
<220> FEATURE:
<223> OTHER INFORMATION: Synthetic Linker

<400> SEQUENCE: 5
aaagcttccg gaggtcccga g                                              21

<210> SEQ ID NO 6
<211> LENGTH: 7
<212> TYPE: PRT
<213> ORGANISM: Artificial Sequence
<220> FEATURE:
<223> OTHER INFORMATION: Synthetic Linker

<400> SEQUENCE: 6

Lys Ala Ser Gly Gly Pro Glu
1               5

<210> SEQ ID NO 7
<211> LENGTH: 29
<212> TYPE: DNA
<213> ORGANISM: Artificial Sequence
<220> FEATURE:
<223> OTHER INFORMATION: Synthetic primer derived from TBP-1

<400> SEQUENCE: 7
catcatatgg atagtgtgtg tccccaagg                                      29

<210> SEQ ID NO 8
<211> LENGTH: 32
<212> TYPE: DNA
<213> ORGANISM: Artificial Sequence
<220> FEATURE:
<223> OTHER INFORMATION: Synthetic primer derived from TBP-1

<400> SEQUENCE: 8
aggaagcttt attctcaatc tgggtaggc ac                                   32

<210> SEQ ID NO 9
<211> LENGTH: 52
<212> TYPE: DNA
<213> ORGANISM: Artificial Sequence
<220> FEATURE:
<223> OTHER INFORMATION: Synthetic primer derived from Pseudomonas
      aeruginosa
```

-continued

```
<400> SEQUENCE: 9
aattaaagct tccggaggtc ccgagggcgg cagcctggcc gcgctgaccg cg        52

<210> SEQ ID NO 10
<211> LENGTH: 33
<212> TYPE: DNA
<213> ORGANISM: Artificial Sequence
<220> FEATURE:
<223> OTHER INFORMATION: Synthetic primer derived from Pseudomonas
      aeruginosa

<400> SEQUENCE: 10
aatgaattct tacttcaggt cctcgcgcgg ggg                              33
```

CHIMERIC PROTEINS AND USES THEREOF

The present application is filed under 35 U.S.C. §371 as a U.S. national phase application of PCT application no. PCT/IL2005/000689, which was filed Jun. 28, 2005. The aforementioned PCT application claimed benefit of priority of U.S. Provisional Application No. 60/582,827, which was filed Jun. 28, 2004. The entire text of each of the aforementioned applications is incorporated herein by reference.

FIELD OF THE INVENTION

The invention relates to compositions and methods for specifically delivering effector molecules to cells expressing ligands of the TNF/NGF family and thereby selectively killing or modifying said cells.

BACKGROUND OF THE INVENTION

Cytokines normally serve to enhance defense. However, when acting in excess, they may cause great damage, not lesser than that which pathogens can cause. In fact, in many diseases unwarranted effects of cytokines constitute a major pathogenic cause.

Cytokines of the TNF family regulate a wide range of different immune defense mechanisms, both of the innate and the adaptive types. Excessive function of several of them, including TNF (Genbank ID X01393) the Fas ligand (TNFSF6, Genbank ID U11821), CD40 ligand (TNFSF5, Genbank ID X67878) and others have been implicated in the pathology of various diseases. There is, in particular extensive evidence for a major pathological role of TNF in a wide range of diseases: infectious diseases such as malaria and sepsis, autoimmune diseases such as rheumatoid arthritis, the inflammatory bowel diseases and psoriasis, and certain types of cancer. Indeed, blocking TNF action by means such as anti-TNF antibodies or soluble TNF receptors was found to provide therapy at such situations [1] [2] [3].

In some pathological situations, including rheumatoid arthritis and Crohn's disease, a rather significant proportion of the patients respond favorably to anti-TNF therapy. There are, however, also patients with such diseases that respond rather poorly to these means, raising the need to define additional approaches for therapy [4].

Unlike many other cytokines that act solely as soluble proteins following their secretion by the cytokine-producing cell, the ligands of the TNF family are (with the exception of lymphotoxin (LTA, Genbank ID X01393) which is produced as a soluble secreted protein) produced as cell-bound type II transmembrane proteins. They can exert their effects in that form, affecting only cells that are located adjacently to the ligand-producing cell (juxtacrine regulation). Most of them are also shed, forming soluble molecules that circulate. Parts of those soluble ligands, for example TNF, are capable of acting as soluble cytokines, serving as paracrine regulators (affecting cells located relatively close to the ligand producing-cells) and endocrine regulators (affecting remote cells). Other ligands of the TNF family, for example the Fas ligand, do not act effectively in their shed form and may in that form even serve as antagonist to the cell-bound form [5] [6].

The occurrence of ligands of the TNF family on the surface of the cells producing them provides a potential means for specific targeting of these ligands producing cells. Such means can allow selective suppression or even elimination of the ligand producing cells at situations where the ligand plays a pathogenic role.

In several respects, destruction of cells producing a cytokine may turn to provide even better defense against the pathogenic effects of this cytokine than just direct blocking of the function of the cytokine molecules:

Destruction of the cytokine-producing cell prevents further synthesis of the cytokines and thus is likely to provide more durable protection than that obtained by just blocking the effect of the cytokine molecules that had been synthesized already.

Cells producing a cytokine often produce simultaneously some other cytokines that together serve to elicit a particular type of immune response. Well-known examples are the Th1- and Th2-type T lymphocytes, lymphocytes that produce distinct groups of cytokines, each serving to elicit a different type of immune defense [7]. Destroying cells producing a cytokine may thus, beside arrest of the synthesis of that particular cytokine, also result in arrest of synthesis of several other cytokines that assist the former in its pathogenic effects.

While blocking circulating cytokines affects the whole body, killing cytokine-producing cells can be restricted to a particular site in the body where these cells reside, thus allowing abolition of the cytokine deleterious effects at that particular site while maintaining beneficial effects of the cytokine at other sites.

Studies of the effect of anti-TNF therapy in Crohn's disease suggest that killing of TNF-producing cells may in some pathological situations indeed provide more effective therapy than that obtained by just blocking TNF. Therapeutic effects of anti-TNF antibodies in this disease were found to correlate with early induction of death of the TNF-producing cells by the antibodies [8] [9] [10]. There is thus a need to design means for effective and selective targeting of cells producing TNF or other ligands of the TNF family.

Cytotoxins joined to targeting molecules that bind to a cell-surface constituents can serve as potent cell-killing agents. Choosing a targeting moiety that recognizes a cell-type specific surface constituent can allow applying such cytotoxic chimera for selective destruction of specific cells in vivo. For example, chimeric fusion proteins comprised of antibodies against cancer-specific epitopes fused to *Pseudomonas* exotoxin (PE) or to Diphtheria toxin (DT) can specifically target and kill cancer cells. Such anti-cancer effects have also been obtained with chimera in which the toxins have been fused to ligands or hormones such as IL2, IL4 or IL13 whose receptors are prevalent in certain tumors. Likewise, cytotoxin-containing chimera were designed to be targeted to pathogen-afflicted cells. For example, HIV-infected cells can be selectively destroyed using immunotoxins comprised of an anti-gp120 antibody directed to the conserved CD4 binding site of gp120, or CD4, attached to a *Pseudomonas* exotoxin [1,1] [1,2] [13].

One kind of possible mean for targeting cytotoxins or other modulating agents to cells that express ligands of the TNF family is antibodies against these ligands. Indeed, antibodies against the CD40 ligand have been applied to target a toxin to CD40 ligand producing cells (Patent # EP1005372). However, only part of the antibodies produced against a particular ligand will bind effectively to the cell-bound form of this ligand, and of those—only part will be capable of competing with receptor molecules (soluble or cell-associated) once they bind to the ligand. Screening for such antibodies may turn to be highly involving and lengthy. Another disadvantage of antibodies, which are usually murine, is that they evoke an immune response in the patient.

It would, therefore, be desirable to define a general approach for generation of proteins that can target effectively cells producing ligands of the TNF family.

SUMMARY OF THE INVENTION

The invention relates to a chimeric protein capable of killing or modifying a cell expressing abnormally high levels of a ligand of a receptor of the TNF/NGF family, comprising the amino acid sequence of at least one polypeptide consisting of an extracellular portion of said receptor or a mutein, fusion protein, functional derivative, a circularly permuted derivative or active fraction thereof, said polypeptide being connected to an effector molecule.

In one embodiment of the invention, the polypeptide of the chimeric protein consists of an extracelullar portion of the TNF receptor, CD27, CD30, CD40 and Fas.

In another embodiment of the invention, the polypeptide of the chimeric protein consists of the extracellular portion of the p55 TNF receptor such as the TNF binding protein-1 (TBPI).

In one aspect of the invention, the effector molecule in the chimeric protein is a cytotoxic molecule such as pseudomonas exotoxin, diphtheria toxin, ricin, abrin, pokeweed antiviral protein, saporin and gelonin, or a fragment thereof.

In one embodiment of the invention, the effector molecule in the chimeric protein is a fragment of pseudomonas exotoxin, such as the fragment herein designated PE, corresponding to the amino acid sequence of SEQ ID NO: 3.

In a further embodiment, the invention provides the chimeric protein having the amino acid sequence of SEQ ID NO: 2, designated herein TBP-PE, or a mutein, fusion protein, functional derivative, a circularly permuted derivative, active fraction or salt thereof.

In one aspect of the invention, the effector molecule in the chimeric protein is a fluorescent composition, a radioactive composition, a mammalian cell death protein such as of Bax, Bak and the DNA fragmentation factor 40, a liposome containing cyclosporine, a cytokine such as an immunosuppressive cytokine, a growth factor, an antibody which may be specific to a tumor cell antigen or an intracellular regulatory protein such as Bclx, a CAD-protein, a caspase and IkB.

In one embodiment, the invention provides an isolated DNA sequence encoding a chimeric protein of the invention for example, nucleotide sequence of SEQ ID NO: 1 or a DNA encoding TBP-PE, or a mutein, fusion protein, functional derivative, a circularly permuted derivative or active fraction thereof, optionally, said isolated DNA further encoding a signal peptide for secretion in eukaryotic cells.

In a further embodiment, the invention provides an expression vector comprising said DNA sequence.

In yet another embodiment the invention provides a host cell comprising said expression vector such. The host cell may be a prokaryotic or eukaryotic cell for example, HeLa, CHO, HEK293, THPI, Yeast, and insect cells.

In one aspect, the invention provides a method for producing a chimeric protein, such as TBP-PE, or a mutein, fusion protein, functional derivative, a circularly permuted derivative or active fraction thereof, comprising culturing said host cell comprising said expression vector, and isolating the chimeric protein produced In another aspect, the invention relates to a pharmaceutical composition comprising a chimeric protein of the invention such as TBP-PE, or a mutein, fusion protein, functional derivative, a circularly permuted derivative, active fraction, or salt thereof, and a pharmaceutically acceptable carrier.

In a further aspect, the invention relates to a pharmaceutical composition comprising said DNA or said vector, both encoding the chimeric protein of the invention, and a pharmaceutically acceptable carrier.

In one embodiment, the invention relates to the use of a chimeric protein of the invention such as TBP-PE, or a mutein, fusion protein, functional derivative, a circularly permuted derivative, active fraction or salt thereof in the manufacture of a medicament for the treatment of a disease.

In one embodiment, the chimeric protein is used in an autoimmune disease.

In another embodiment of the invention, the chimeric protein is used in a disease in which a ligand of a receptor of the TNF/NGF family, such as TNF, is involved in the pathogenesis and/or the course of the disease, for example acute disease such as septic shock, graft-versus-host disease, malaria, infectious hepatitis and tuberculosis or chronic disease such as chronic graft-versus-host disease, rheumatoid arthritis, juvenile diabetes, cancer associated cachexia, inflammatory bowel disease (IBD) and psoriasis.

In yet another embodiment of the invention, the chimeric protein is used in cancer, and said chimeric protein binds to the ligand of a receptor of the TNF/NGF family expressed by the cancer cells. For example, the chimeric protein that comprises the extracellular portion of a TNF receptor can be used in cancer of epithelial origin such as breast cancer expressing TNF.

In yet another embodiment, the invention relates to the use of the chimeric protein of the invention in the manufacture of a medicament for treatment of stem cells of a cancer patient prior to autologous transplantation, for killing harmful cells expressing the ligand to which the chimeric protein binds. For example, the chimeric protein may be administered to the patient prior to removal of the stem cells or may be used to treat the cells removed from the patient and prior to transplantation.

In yet another embodiment, the invention relates to the use of TBP-PE, or a mutein, fusion protein, functional derivative, a circularly permuted derivative, active fraction or salt thereof in the manufacture of a medicament for the treatment of a disease, wherein epithelial cells expressing TNF are involved in the pathogenesis and/or the course of the disease. For example, in diseases such as breast cancer, graft-versus-host disease (GVH), psoriasis and inflammatory bowel diseases (IBDs) such as Crohn's or ulcerative colitis.

In one aspect, the invention provides a method of treatment of an autoimmune disease, comprising administering to a subject in need a therapeutically effective amount of a chimeric protein of the invention such as TBP-PE or a mutein, fusion protein, functional derivative, a circularly permuted derivative, active fraction or salt thereof.

In another aspect, the invention provides a method of treatment of a disease in which the activity of a ligand of a receptor of the TNF/NGF family, e.g. TNF, is involved in the pathogenesis or in the course of said disease, comprising administering to a subject in need a therapeutically effective amount of a chimeric protein of the invention such as TBP-PE or a mutein, fusion protein, functional derivative, a circularly permuted derivative, active fraction or salt thereof. For example, TNF is involved in the pathogenesis and/or in the course of the following diseases: acute disease such as septic shock, graft-versus-host disease, malaria, infectious hepatitis and tuberculosis or chronic diseases such as chronic graft-versus-host, rheumatoid arthritis, juvenile diabetes, cancer associated cachexia, inflammatory bowel disease (IBD) and psoriasis.

In one embodiment, the invention provides a method of treatment of a cancer in which the cancer cells express a ligand of a receptor of the TNF/NGF family, e.g. TNF, comprising administering to a subject in need a therapeutically effective amount of a chimeric protein of the invention such as TBP-PE, or a mutein, fusion protein, functional derivative, a circularly permuted derivative, active fraction or salt thereof.

In a further embodiment of the invention, said cancer is of epithelial origin, for example, breast cancer.

In another embodiment, the invention relates to a method for killing bone marrow harmful cells expressing TNF prior to autologous transplantation, comprising administering to a subject in need a therapeutically effective amount of a chimeric protein of the invention. For example, the chimeric protein may be administered to the subject in need prior to the removal of the bone marrow cells.

In yet another embodiment, the invention provides a method of treatment of a disease, such as breast cancer, graft-versus-host disease, psoriasis and inflammatory bowel disease, in which epithelial cells expressing TNF are involved in the pathogenesis and/or the course of the disease said disease, comprising administering to a subject in need a therapeutically effective amount of TBP-PE, or a mutein, fusion protein, functional derivative, a circularly permuted derivative, active fraction or salt thereof.

BRIEF DESCRIPTION OF THE FIGURES

FIGS. 1A-B show schematic representations of the TBP-PE chimeric protein (FIG. 1A) and the *Pseudomonas* exotoxin (FIG. 1B). *Pseudomonas* exotoxin (FIG. 1B) enters the cells by receptor-mediated endocytosis and is cleaved by a cellular protease (Furin-like) to produce a 40 kDa fragment (PE), containing translocating and ADP-ribosylating activity. After proteolysis, PE reaches the endoplasmic reticulum, is translocated to the cytosol and inhibits protein synthesis by ADP-rybosylation of elongation factor 2 (EF2). The TBP-PE chimeric protein (FIG. 1A) comprises TBPI or TNF-binding protein 1 (extracellular portion of the p55 TNF receptor) and the PE fragment of *Pseudomonas* exotoxin.

FIGS. 1C-D show the DNA sequence (FIG. 1C SEQ ID NO: 1) encoding the chimeric TBP-PE protein and the corresponding amino acid sequence (FIG. 1D SEQ ID NO: 2).

FIGS. 1E-F show the DNA sequence of PE (FIG. 1E, SEQ ID NO: 3), the fragment encoding domains II and III of *Pseudomonas* exotoxin and the corresponding amino acid sequence (FIG. 1F, SEQ ID NO: 4).

FIGS. 1G-H show the DNA sequence of the linker peptide connecting TBPI and PE moieties (FIG. 1G, SEQ ID NO: 5) and the corresponding amino acid sequence (FIG. 1H, SEQ ID NO: 6).

Figure 6A:
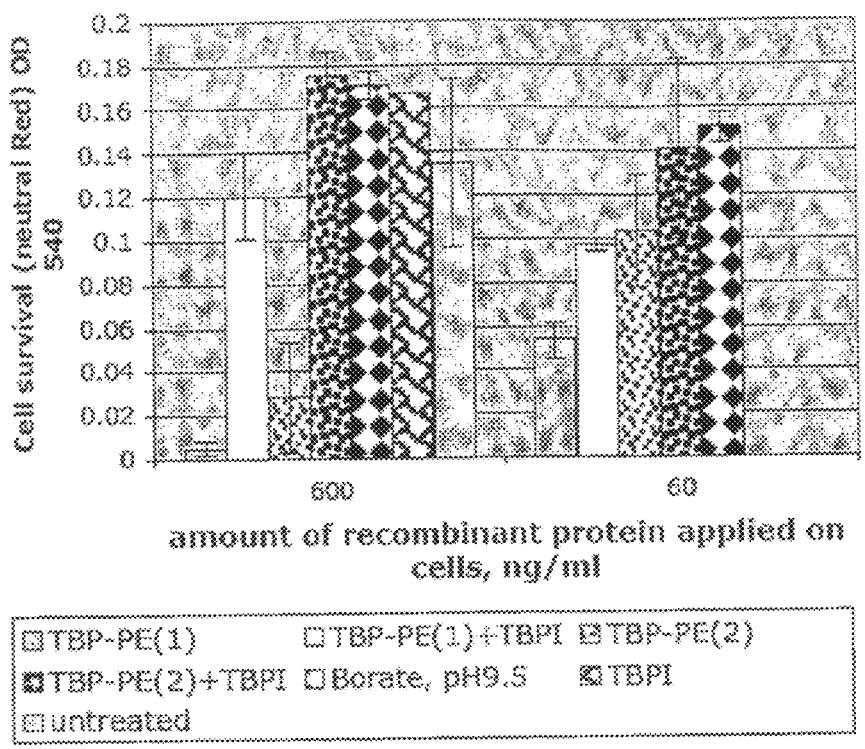
FIGS. 6 A-D show that TBP-PE is cytotoxic to cells overexpressing membrane bound TNF and particularly to cells overexpressing membrane bound TNF of epithelial type. The cytotoxic activity of TBP-PE was tested in epithelial HeLa cells or in HeLa-M9 cell line engineered to overexpress surface TNF (Pocsik et al., 1995) (FIG. 6A), in an activated monocytic-like cell line (FIG. 6B) or in activated primary macrophage cells (FIG. 6C). The cells were seeded in 96-well plates and were treated with the indicated concentrations of TBP-PE or TBPI (as a control). Growth and viability of the cells after 24 hours of treatment was assessed as indicated in Example 7. In some wells the cells were treated with the combination of TBPI and TBPI-PE to assess specificity of TBPI-PE cytotoxicity through binding cell surface TNF-α. We found that 60 and 600 ng/ml of two different batches of TBP-PE had cytotoxic effect on HeLaM9 and that the cytotoxic effect was specifically induced trough the membrane bound TNF-α since cytotoxicity was completely inhibited by competition with TBP-1 (FIG. 6A).
Figure 6B:
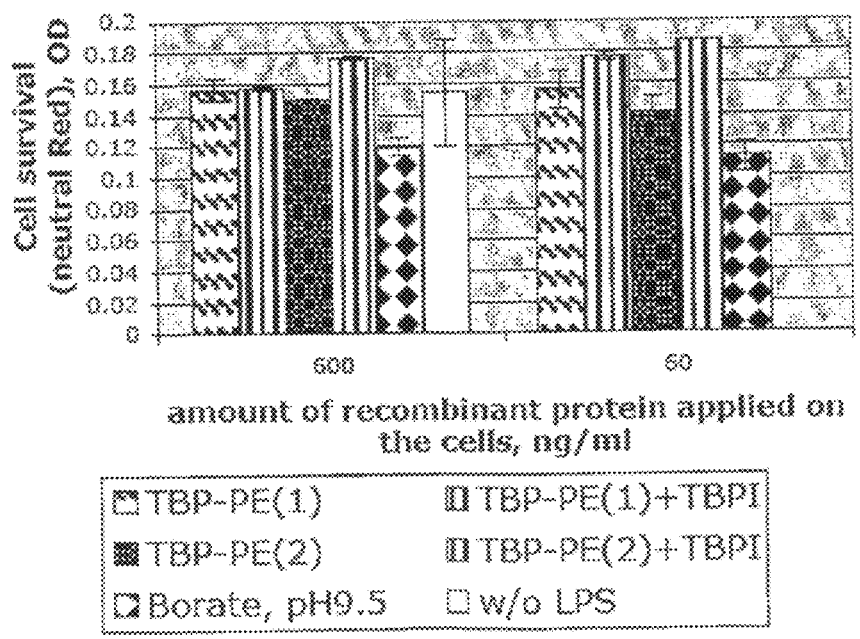
Figure 6C:
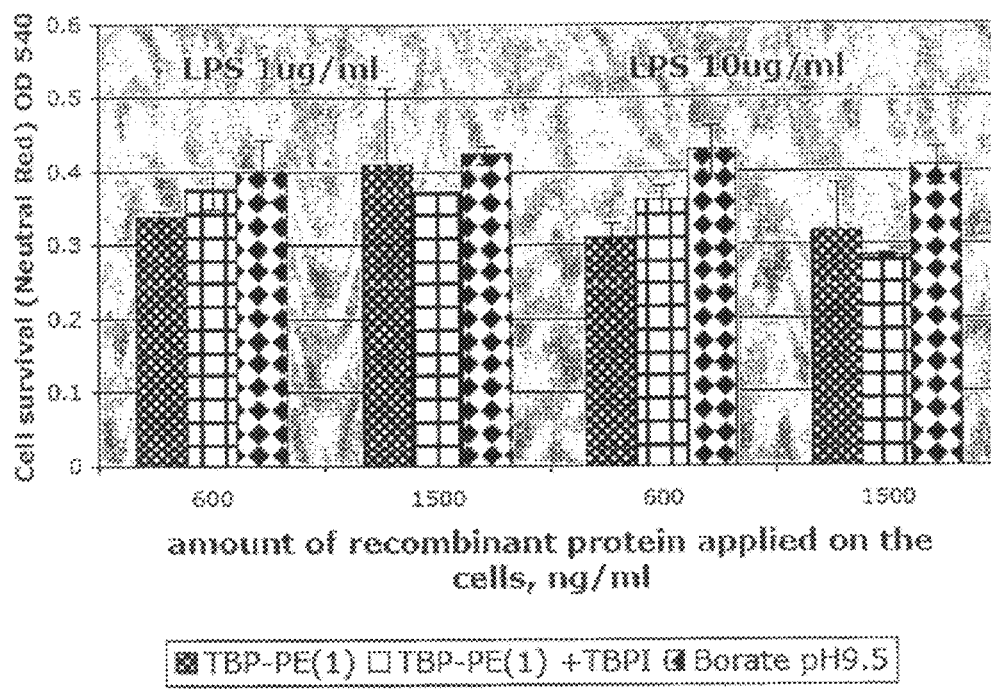

We found that the same concentrations of TBP-PE which induced cytotoxicity in the epithelial cell line HeLaM9 were not cytotoxic for the activated monocytic-like THPI cell line (FIG. 6B) or for primary macrophages activated by treatment with E. coli with 1 or 10 ng LPS (FIG. 6C).

Figure 6D:
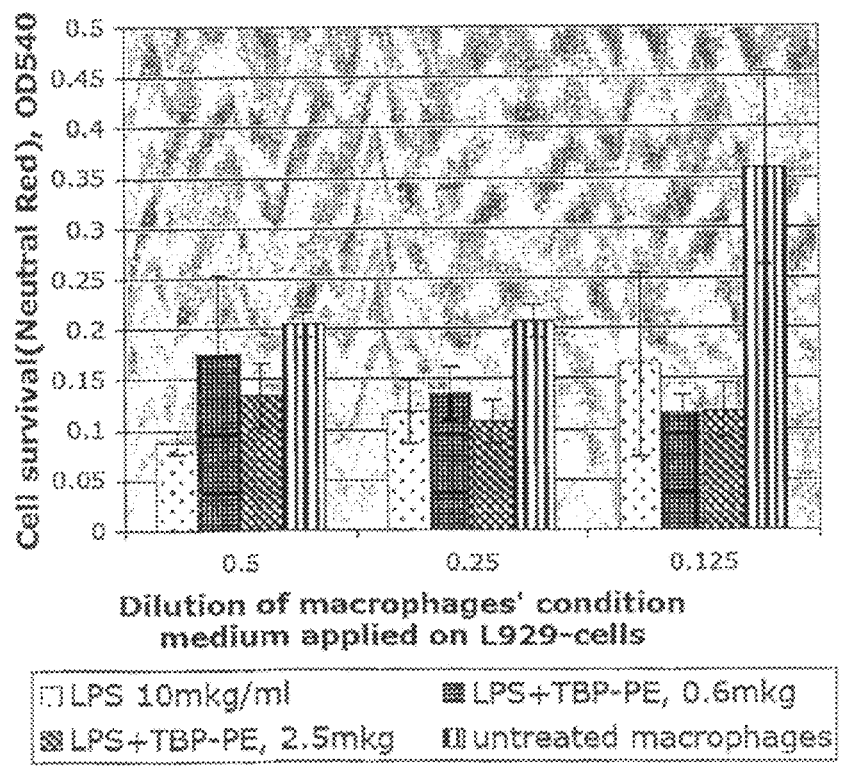

The effect of TBP-PE on the secretion of TNF by activated macrophages was also explored (FIG. 6D). The culture medium of activated macrophages treated with TBP-PE at concentrations of 600 and 1500 ng/ml or untreated, was collected and diluted two, four and eight folds with fresh medium, and applied to L929 cells, and TNF dependent death of the cells indicative of the TNF concentration, was monitored. We found that TNF secretion by activated macrophages was not inhibited by TBP-PE.

Figure 7:
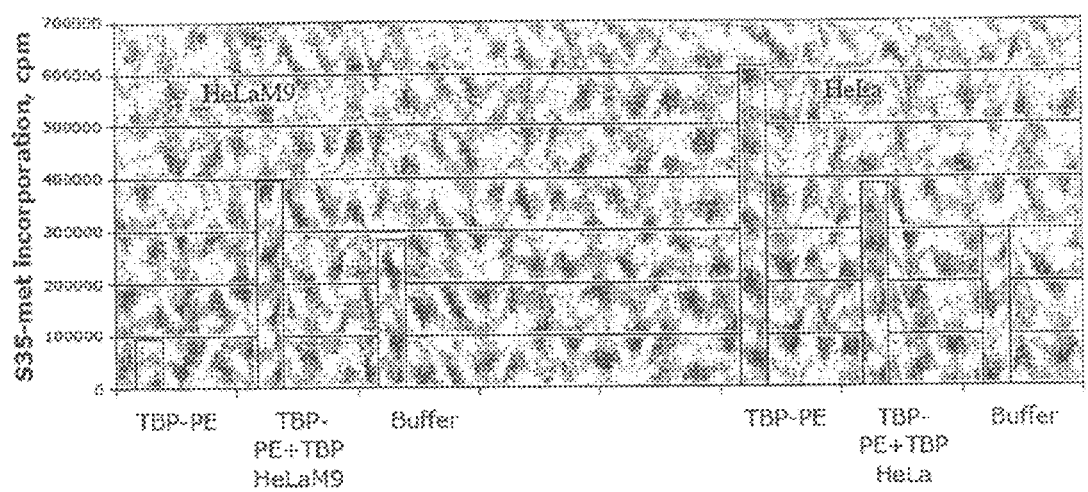

FIG. 7 shows that TBP-PE inhibits protein synthesis in HeLaM9 cells. HeLaM9 and HeLa cells were treated with (600 ng/ml) TBP-PE or remained untreated ("Buffer") and were subjected to radioactive label with of $^{35}$S-Met. In one experimental group, TBPI was applied to the cells simultaneously with TBPI-PE ("TBP-PE+TBP") to compete for cell surface TNF. After treatment, the cells were lysed and radioactivity of TCA-precipitated protein was measured as described in Example 8. The Figure shows that 600 ng/ml of TBP-PE inhibited protein synthesis in HeLa-M9 for at least 75% cells but did not impair protein synthesis in HeLa cells. TBPI completely inhibited inhibitory the effect of TBP-PE in HeLa-M9 when added at a 10-fold excess. TBPI alone did not affect protein synthesis neither in HeLa-M9, nor in HeLa cells.

DETAILED DESCRIPTION OF THE INVENTION

The invention relates to a chimeric protein capable of killing or modifying a cell expressing abnormally high levels of a ligand of a TNF/NGF receptor, comprising the amino acid sequence of at least one polypeptide consisting of an extracellular portion of said TNF/NGF receptor, or a mutein, fusion protein, functional derivative, a circularly permuted derivative, or active fraction thereof connected to an effector molecule selected from the group consisting of a cytotoxic, regulatory and reporter molecule.

The present invention allows targeting (or specifically delivering) an effector molecule to cells expressing a cell-bound ligand of the TNF/NGF family.

The present invention is based on results obtained with a chimeric protein, herein designated TBP-PE, corresponding to the amino acid sequence in SEQ ID NO: 2 (FIG. 1D), comprising the soluble form of the p55 TNF receptor (TBPI) and, as the effector molecule, a polypeptide comprising the translocating and ADP-ribosylation domains of Pseudomonas exotoxin. The experimental results demonstrated that TBPI-PE has essentially the same TNF-binding activity as TBPI, that it penetrates only into cells expressing cell surface TNF-αc causing inhibition of protein synthesis only in these cells, and consequently cell death.

The chimeric gene TBP-PE comprising the extracellular portion of the p55 TNF receptor (TBPI) and a 40 kDa fragment of Pseudomonas exotoxin (PE), containing domains II, Ib and III of Pseudomonas exotoxin was prepared by PCR amplification. The TBP-PE protein was produced in the prokaryotic cell BL21 transformed with the TPB-PE vector (pTBP-PE). The inclusion bodies, containing most of the recombinant protein were dissolved in denaturation solution and re-natured. The refolded TBP-PE protein produced in bacterial cells had the correct size of 57 kDa.

The refolded TBP-PE was further purified by affinity chromatography with an anti TBP-I cross-linked.

The ADP-rybosilation activity of the refolded TBP-PE protein was explored in vitro. ADP-ribosylation of EF2 was induced by the refolded TBP-PE protein (from denatured inclusion bodies of Example 2). The level of EF2 ADP-ribosylating activity of the refolded protein increased with the amount of refolded TBP-PE used in the reaction.

Quantitation of refolded TBP-PE was estimated by Enzyme-Linked Immunosorbent Assay (ELISA) using antibodies specific for TBPI. In addition TNF binding activity of refolded TBP-PE was compared to the TNF binding activity of purified TBPI produced in CHO cells to TNF. We found that the concentration of TBP-PE estimated by ELISA was similar to the one found by Bradford demonstrating that refolded TBP-PE and TBPI are recognized by anti-TBPI antibodies with similar efficiently. The binding of the same amount (as measured by ELISA) of TBPI (purified from eukaryotic cells) or refolded TBPI-PE to TNF was explored in TNF coated plates. We found using the activity of TBPI as 100% TNF binding that at least 50% of refolded TBP-PE had TNF binding activity.

The cytotoxic activity of the fusion protein TBP-PE (and as control the soluble TNF receptor alone) was tested in epithelial or in monocytic-like LPS-treated cells. HeLa-M9 cells is a clone of the epithelial HeLa cervical carcinoma line that constitutively expresses under the control of the SV40 promoter a human TNF mutant cDNA in which the arginine at position +2 and the serine at position +3 are substituted for threonines. These mutations cause about tenfold reduction in the cleavage rate of 26 kDa surface TNF. The cells are cultured in RPMI 1640 medium supplemented with 10% Fcs, 2 mM L-glutamine, 100 mg/ml penicillin, 100 mg/ml streptomycin and 50 mg/ml gentamycin.

The HeLa-M9 (overexpressing membrane bound TNF), or HeLa cells were seeded in 96-well plates and incubated with different concentrations of TBP-PE or TBPI and viability of the cultures was assessed using Neutral Red stain. To some wells TBPI was applied simultaneously with TBPI-PE to compete for TNF in order to check specificity of TBP-PE action induced through membrane-bound TNF-α.

We found that 600 ng/ml of TBP-PE caused death of at of HeLa-M9 cells, overexpressing TNF-α on their surface, but did not affect HeLa cells. TBPI blocked specifically the cytotoxic effect of TBP-PE, when applied in 10-fold excess. TBPI alone did not cause cytopathic effect at concentrations of up to 76 mg/ml. Two different batches of TBP-PE were tested and were found to be similarly cytotoxic for HeLa-M9 cells. TBP-PE caused more than 90% cell death in HeLaM9 cells at concentrations of 600 ng/ml. One of the batches of TBP-PE was very active and was cytotoxic at concentrations as low as 0.06 mg/ml, killing nearly 65% of HeLaM9 cells.

TBP-PE was found to dramatically inhibit the protein synthesis in HeLa-M9 but to lack of any inhibitory effect in protein synthesis of HeLa cells. TBPI was found to inhibit the effect of TBP-PE in HeLa-M9 cells when added together with TBP-PE at 10-fold excess. TBPI alone did not affect the synthesis of proteins in HeLa-M9 or in HeLa cells.

The effect of TBP-PE was explored also on an activated monocytic-like cell line (THPI) or activated primary macrophages both, overexpressing cell surface TNF. We found that TBP-PE, tested at concentrations causing cytotoxicity on HeLaM9 cells (60 and 600 ng/ml), lacked cytotoxic activity on activated THPI line and on activated primary macrophages, and did not inhibit TNF secretion in the later cells, demonstrating that the cytotoxic effect of TBP-PE is specific for epithelial cells overexpressing cell bound TNF.

In one embodiment of the invention, it was shown that TBP-PE is cytotoxic for epithelial tumor cells overexpressing membrane TNF, such as HeLa M9 but is not cytotoxic for activated cell lines resembling monocytes or activated cultures of primary macrophages both, overexpressing membrane TNF.

Diebel et al. (J. Trauma. 2005 58 (5): 995-1001) indicated that apoptosis of intestinal epithelial cells might contribute to intestinal failure after low-flow conditions to the gut. Diebel at al. shown that the epithelial Caco2 intestinal cell line after exposed to combined insults such as bacteria and hypoxia-reoxygenation produced TNF which in turn induced apoptosis in these.

Therefore, TBP-PE may be used to specifically kill intestinal epithelial cells overexpressing TNF which contribute to apoptosis in conditions of the gut such as the bowel inflammatory diseases (BID) ulcerative colitis and Crohn's.

Konour et al. (Br J. Dermatol. 2005; 152(6): 1134-42) indicated that apoptosis of keratinocytes or of intestinal epithelial cells is an important pathophysiological mechanism of organ damage during acute graft-versus-host (GVH) disease. Konour et al. explored the mediators responsible for inducing apoptosis in GVH in an in-vitro model of GVH comprising keratinocyte or human skin explant cultures, each one mixed with major hystocompatibility complex mismatched lymphocyte cultures. The results obtained by Konour et al. show that IFN gamma and TNF produced by keratinocytes and human skin explant cultures are mediators of apoptosis in GVH.

Therefore TBP-PE may be administered to patients receiving a transplant in order to specifically kill keratinocytes or intestinal epithelial cells producing TNF to prevent or minimize the GVH.

Both keratinocytes and T cells secrete substantial amounts of TNFα in psoriasis, the prevalent importance of one of these types of cells in pathogenesis of the disease is not clear (Kupper T. S., Immunologic Targets in Psoriasis. N. Engl. J. Med., 2003, v. 349, pp. 1987-1990; Asadullah K. et al., Novel Immunotherapies for psoriasis. TRENDS in Immunology, 2002, v. 23, Nol, pp. 47-53) Hong K. et al. shows that IL-12, independently of INF-gamma, plays a crucial role in the pathogenesis of a murine psoriasis-like skin disorder. J. Immunology, 1999, v. 162; pp. 7480-7491). Hong et al. indicated that skin-derived inflammatory cells of interferon gamma-/- phenotype secreted substantially amounts of TNF-α in mice, but not in the presence of anti IL-12.

Therefore TBP-PE may be administered to psoriatic patients in order to specifically kill skin derived inflammatory cells producing TNF.

Stuelten et al. (J Cell Sci. 2005 15; 118 (Pt10), 2143-53) explored tumor-stroma interactions in the mechanism of increasing the malignancy potential of breast cancer cells. For this purpose Stuelten used 2D-cocultures including fibroblasts (e.g. stroma cells) and human tumor breast epithelial cells of increasingly malignant potential. Stuelten at al. showed that the expression of MMP-9 (known to facilitate tumor metastasis) in fibroblasts is induced by the action of TNF-α and TGF-beta secreted by the tumor.

Therefore TBP-PE may be used to effectively kill epithelial breast cancer or other cancer of epithelial origin producing TNF-α in order to prevent tumor growth and metastasis.

In all, the results obtained with TBP-PE, showing a specific effect only on cells overexpressing membrane bound TNF, demonstrate that TBP-PE as well as other chimeric protein of the invention can be exploited for therapeutical purposes.

According to the present invention, a highly effective and selective general mean for targeting the ligands of the TNF family is provided by the extracellular portion of the receptors to which they bind. Several of the receptors for these ligands exist naturally not only in cell-bound form but also in a soluble form that corresponds to the extracellular portion or domains of these receptors. Some of these soluble forms have been shown to bind effectively to their respective ligands, to an extent that allows them to block the interaction of the ligands with their cell surface receptors. Moreover, certain receptors of the TNF/NGF family (e.g. OPG (TNFRSF11B, Genbank ID U94332) are produced only as soluble molecules and in that form block effectively the binding of the ligand with which they interact to other, cell surface, receptors of the family.

The extracellular portion of the receptors of the TNF/NGF receptor family such as TNF receptor, CD27, CD30, CD40 and Fas are contemplated according to the present invention. Chimeric molecules including soluble forms of receptors of the TNF family may be fused to other moieties to maintain the ability of the soluble receptor to target them to specifically cell-bound ligand molecules. Besides, they may possess some additional activities endowed by the moiety to which the soluble receptor has been fused, e.g. the fusion of the soluble forms of the TNF receptors to the Fc portion of immunoglobulin or polyethylene glycol may endowed the chimera with a longer clearance time than that of the original soluble receptor molecules. The fusion of two soluble receptor molecules to an Fc portion of an immunoglobulin molecule also may confer to these receptor molecules a greater effectiveness of binding to their ligand.

"Effector molecules" are proteins or chemicals that when placed at proximity or inside of the target cell can impose on it a desired functional or phenotypic change. Functional changes in cells include, without being limited to, cell death and down regulation of ligand expression. A phenotypic change include, without being limited to, changes in cell fluorescence and radioactivity.

In one embodiment, the extracellular portion of the TNF/NGF receptor is fused (or connected) to an effector molecule which is a native or modified cytotoxin such as *Pseudomonas* exotoxin (PE), Diphtheria toxin (DT), ricin, abrin, pokeweed antiviral protein, saporin, gelonin and the like.

In another embodiment, the extracellular portion of the receptor can be fused (or connected) to a mammalian cell-death protein, for example the Bcl2-related proteins Bax or Bak, or DNA Fragmentation Factor 40 [14].

In another embodiment, the effector molecule may be a pharmacological agent or a vehicle containing a pharmacological agent. The extracellular portion of the TNF/NGF receptor may be linked for example to a fluorescent composition, allowing imaging of the cells producing the ligand to which this receptor binds. It may also be linked to a radioactive compound, which may also be used for imaging of the ligand-producing cells as well as for their destruction. Linking the soluble receptor to a liposome-containing cyclosporine, a drug that affects preferentially activated T-lymphocytes, will allow selective inhibition of the function of T lymphocytes that produce the ligand recognized by the receptor.

In yet another embodiment, the effector molecule may be a growth factor, or a cytokine. It may for example be an immunosuppressive cytokine, allowing specific delivery of this cytokine to cells expressing the ligand for the receptor.

In still yet another embodiment, the effector molecule may be an antibody, for example—an antibody to a tumor-cell specific antigen. A chimera comprised of such an antibody and a soluble receptor for TNF will prompt association of the TNF-producing cells with the tumor cells and thus dictate destruction of the tumor cells by TNF.

In another embodiment, the effector molecule may be an intracellular regulatory protein such as Bclx, CAD-protein, a caspase such as caspase-8 and IκB.

Natural occurrence of soluble forms of receptors has been described for almost all members of the TNF/NGF family, including the two receptors of TNF (TNFR55 and TNFR75), CD27, CD30, Fas and others. The chimeric protein will include either a naturally occurring or artificial soluble forms of a receptor of the family. It can be the whole extracellular domain of any particular receptor of the TNF/NGF family or a mutein, fusion protein, functional derivative, a circularly permutated derivative or active fraction thereof.

The terms "chimeric protein" and "conjugate" are interchangeable in the specification.

As used herein the term "muteins" refers to analogs of a protein, in which one or more of the amino acid residues of the naturally occurring components of the protein are replaced by different amino acid residues, or are deleted, or one or more amino acid residues are added to the original sequence of the protein, without changing considerably the activity of the resulting products as compared with the original protein. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes the protein, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12° 20-° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of the soluble receptor of the invention, such as to have substantially similar, or even better, activity to the proteins of the invention. For example, one characteristic activity of TBP is its capability of binding to TNF. An ELISA type assay for measuring the binding of TNF is described in the examples below. As long as the mutein has substantial binding activity to the soluble receptor of the invention, it can be considered to have substantially similar activity to soluble receptor of the invention. Thus, it can be determined whether any given mutein has at least substantially the same activity as the soluble receptor by means of routine experimentation comprising subjecting such a mutein, e.g., to a simple binding assay to determine whether or not it binds to its ligand, as described for TBP and TNF in the examples below.

In a preferred embodiment, any such mutein has at least 40% identity or homology with the amino acid sequence of TBP. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1): 387-95.), for example the programs BESTFIT and GAP, may be used to determine the % identity between two polynucleotides and the % identity and the % homology between two polypeptide sequences. BESTFIT uses the "local homology" algorithm of Smith and Waterman (J Theor Biol. 1981 Jul. 21; 91(2): 379-80 and J Mol. Biol. 1981 Mar. 25; 147(1): 195-7. 1981) and finds the best single region of similarity between two sequences. Other programs for determining identity and/or similarity between sequences are also known in the art, for instance the BLAST family of programs (Altschul S F et al, 1990 J Mol. Biol. 1990 Oct. 5; 215(3): 403-10, Proc Natl Acad Sci USA. 1990 July; 87(14): 5509-13, Altschul S F et al, Nucleic Acids Res. 1997 Sep. 1; 25(17): 3389-402, accessible through the home page of the NCBI at www.ncbi.nlm.nih.gov) and FASTA (Pearson W R, Methods Enzymol. 1990; 183:63-98. Pearson J Mol. Biol. 1998 Feb. 13; 276(1): 71-84).

Muteins of a soluble receptor, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of the soluble receptor of the invention may include synonymous amino acids within a group which have sufficiently similar physicochemical properties that substitution between members of the group will preserve the biological function of the molecule (Grantham Science. 1974 Sep. 6; 185(4154): 862-4). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of soluble receptor of the invention, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

"Functional derivatives" as used herein cover derivatives of soluble receptor of the invention, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of the soluble receptor of the invention, and do not confer toxic properties on compositions containing it.

"Functional derivatives" also comprise multimers made up of the soluble receptors in which changes have been introduced in the sequence of the amino acids making up the soluble receptors by any conventional method. These changes may comprise elongation or truncation of the soluble receptor molecule or deletion or replacement of one or more amino acids making up the soluble receptors. It is understood that none of the above changes may affect the binding properties of the soluble receptors.

These derivatives may, for example, include polyethylene glycol side-chains, which may mask antigenic sites and extend the residence of soluble receptor of the invention in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

An "active fraction" according to the present invention may e.g. be a fragment of the soluble receptor of the invention. The term fragment refers to any subset of the molecule, that is, a shorter peptide that retains the desired biological activity e.g. binding the ligand. Fragments may readily be prepared by removing amino acids from either end of the soluble receptor molecule and testing the resultant fragment for its properties to bind to TNF. Proteases for removing one amino acid at a time from either the N-terminal or the C-terminal of a polypeptide are known, and so determining fragments, which retain the desired biological activity, involves only routine experimentation.

As active fractions of the soluble receptor of the invention, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to the soluble receptor of the invention.

In yet a further embodiment, the substance according to the invention comprises an immunoglobulin fusion, i.e. the molecules according to the invention are fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the chimeric protein. The resulting fusion protein ideally has improved properties, such as an extended residence time in body fluids (half-life), increased specific activity, increased expression level, or facilitated purification of the fusion protein.

Preferably, the substance according to the invention is fused to the constant region of an Ig molecule. It may be fused to heavy chain regions, like the CH2 and CH3 domains of human IgG1, for example. Other isoforms of 1 g molecules are also suitable for the generation of fusion proteins according to the present invention, such as isoforms IgG2 or IgG4, or other Ig classes, like IgM or IgA, for example. Fusion proteins may be monomeric or multimeric, hetero- or homomultimeric.

The term "salts" herein refers to both salts of carboxyl groups and to acid addition salts of amino groups of the soluble receptor molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of TBP, i.e., the ability to bind to TNF.

The term "circularly permuted" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The particular circular permutation of a molecule is designated by brackets containing the amino acid residues between which the peptide bond is eliminated. Circularly permuted molecules, which may include DNA, RNA and protein, are single-chain molecules, which have their normal termini fused, often with a linker, and contain new termini at another position. See Goldenberg, et al. J. Mol. Biol., 165: 407-413 (1983) and Pan et al. Gene 125: 111-114 (1993), both incorporated by reference herein. Circular permutation is functionally equivalent to taking a straight-chain molecule, fusing the ends to form a circular molecule, and then cutting the circular molecule at a different location to form a new straight chain molecule with different termini. Circular permutation thus has the effect of essentially preserving the sequence and identity of the amino acids of a protein while generating new termini at different locations.

The procedure for attaching the soluble receptor to the effector molecule will vary according to the chemical structure of the latter. In a preferred embodiment, the effector molecule will be a protein and its fusion (or connection) to the targeting soluble receptor will be preferably done by recombinant means. The genes encoding the two proteins can be isolated as cDNA or in genomic form by any cloning procedure known to those skilled in the art. The soluble receptors and effector proteins can also be linked chemically. This can be done using bifunctional linker molecules such as those available from Pierce Chemical Company, Rockford Ill. (for example BS3 (Bis [sulfosuccinimidyl] suberate).

The coupling (or connecting) between the soluble receptor and the effector molecule may be direct or trough a linking molecule and/or spacer which can be any kind of linker e.g. an amino acid, a peptide or polypeptide, a sulphidril group, a polymer etc.

The linker can be a molecule that may be broken upon localization or internalization of the chimera.

In one embodiment, chimeric proteins of the present invention are synthesized (or produced) using recombinant DNA methodology. Generally this involves creating a DNA sequence that encodes the chimeric protein, optionally encoding also a signal peptide for secretion in eukaryotic cells, placing the DNA in an expression cassette under the control of a particular promoter, expressing the protein in recombinant cultured host cells such as eukaryotic cells (e.g. HeLa cell, CHO cell, HEK293, THPI, Yeast cell and insect cell) or prokaryotic cells (e.g. E. coli cell), isolating the expressed protein and, if required, renaturing the protein.

The nucleic acid sequences encoding the chimeric proteins may be expressed in a variety of host cells. In the case of chimeric proteins containing a cytotoxic moiety a host cell that is resistant to the cytocidal effect of the cytotoxic moiety will be chosen.

Once expressed, the recombinant chimeric proteins can be purified according to standard procedures of the art, including ammonium sulfate precipitation, affinity columns, column chromatography, gel electrophoresis and the like.

After expression and purification, the chimera may possess a conformation substantially different than the native conformations of the constituent polypeptides. In this case, it may be necessary to denature and reduce the polypeptide and then to cause the polypeptide to re-fold into the preferred conformation.

Denaturation is achieved by exposing the crude material containing the recombinant protein to a combination of chaotropic agents (e.g. urea<or guanidine HCl), reducing agent and high pH. These conditions usually cause solubilization and denaturation of proteins in inclusion bodies. Consequently, a clear solution of proteins is obtained. The proteins, at this stage, are completely opened with no secondary or tertiary structures. The next step is to moderate the extreme conditions of pH, reducing agent and chaotropic agent concentration to enable the folding of the protein. The ability of a protein to fold to its native tertiary structure is dictated by its primary structure. Therefore, lowering the chaotropic and reducing agents concentration and reducing the pH is usually sufficient. However, sometimes fine-tuning of the conditions is required.

The invention provides a pharmaceutical composition comprising a chimeric protein of the invention such as TBP-PE, or a mutein, fusion protein, functional derivative, a circularly permuted derivative, active fraction, or salt thereof and a pharmaceutically acceptable carrier.

The invention provides a pharmaceutical composition comprising a DNA or an expression vector encoding the protein of the invention such as TBP-PE, or a mutein, fusion protein, functional derivative, a circularly permuted derivative, active fraction, or salt thereof and a pharmaceutically acceptable carrier.

The recombinant chimeric proteins and pharmaceutical compositions comprising a chimeric protein of this invention are particularly useful for parenteral administration, i.e., subcutaneously, intramuscularly or intravenously. The compositions for parenteral administration will commonly comprise a solution of the chimeric protein or a cocktail thereof dissolved in an acceptable carrier, preferably an aqueous carrier. A variety of aqueous carriers can be used, e.g. water, buffered water, 0.4% saline etc.

The substance can be administered to a patient in need thereof in a variety of ways. The routes of administration include intraliver, intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the chimeric protein is administered to the patient (e.g. via a vector), which causes the chimeric protein to be expressed and secreted in vivo. In addition the substance can be administered together with other components of biologically active agents such as pharmaceutically acceptable surfactants, excipients, carriers, diluents and vehicles.

For parenteral (e.g. intravenous, subcutaneous, intramuscular) administration, the chimeric protein can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The definition of "pharmaceutically acceptable" is meant to encompass any carrier, which does not interfere with effectiveness of the biological activity of the active ingredient and that is not toxic to the host to which it is administered. For example, for parenteral administration, the substance may be formulated in a unit dosage form for injection in vehicles such as saline, dextrose solution, serum albumin and Ringer's solution.

It is a further object of the present invention to provide for a method for treating a disease, comprising administering to a patient in need thereof a chimeric protein such as TBP-PE, or a mutein, fused protein, functional derivative, active fraction, circularly permutated derivative or salt thereof optionally together with a pharmaceutically acceptable carrier.

Single or multiple administrations of the compositions may be administered depending on the dosage and frequency as required and tolerated by the patient. The concentration of chimeric molecule in these formulations will be so designed as to deliver in the body an amount of molecules sufficient for obtaining a therapeutic effect. In the case of autoimmune diseases, the composition will be designed such as to deliver an amount of chimera that is sufficient to affect the course and severity of the autoimmune disease and to improve the patient's condition, leading to reduction or remission of the disease. The effective amount will depend on the route of administration, the disease to be treated and the condition of the patient.

Among various uses of the chimeric proteins of the present invention are in the manufacture of a medicament for the treatment of a disease such as a disease or condition caused by specific human cells that can be eliminated by the toxic action of the protein. One application is the treatment of diseases in which TNF plays a pathogenic role or is involved in the course of the disease (e.g. TNF aggravate the disease) including acute diseases, such as septic shock, graft-versus-host disease (GVHD), malaria, infectious hepatitis, tuberculosis, as well as chronic diseases, such as cancer-associated cachexia, chronic GVHD, rheumatoid arthritis, juvenile diabetes, the inflammatory bowel diseases and psoriasis. Another application is for the treatment of cancer, caused by malignant cells expressing the ligand to which the chimeric protein binds. The chimeric proteins may also be used in vitro or in vivo, for example for the elimination of harmful cells from bone marrow or from mobilized peripheral blood cells before autologous transplantation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The present invention will now be described in more detail in the following non-limiting examples and the accompanying drawings.

EXAMPLES

Example 1

Construction of a Chimeric Gene (Referred Herein TBP-PE) Comprising the Extracellular Portion of the p55 TNF Receptor (TBPI) and a 40 kDa Fragment of *Pseudomonas* Exotoxin (PE), Containing Domains II, Ib and III of *Pseudomonas* Exotoxin In order to prepare the chimeric TBP-PE gene (FIG. 1C, SEQ ID NO: 1), as schematically represented on FIG. 1A, each of the DNA fragments encoding TBP (extracellular portion of the p55 TNF receptor) and PE (a 40 kDa fragment of *Pseudomonas* exotoxin), containing domains II, Ib and III of *Pseudomonas* exotoxin) were amplified by polymerase chain reaction (PCR) amplification and fused.

The amino acid sequence of the soluble form of the p55 TNF receptor (TNFRSF1A, Genbank ID M75866) corresponds to that of the major species of the soluble form of this receptor (TBPI) that had been isolated from human urine (U.S. Pat. No. 5,811,261) and it extends from Asp 41 to Asn 201 in the receptor's extracellular domain (Swiss-Prot accession number: P19438).

TBPI, was isolated by PCR (1) amplification (with High fidelity Taq polymerase from Boehringer Mannheim) using full length TNFR1 (plasmid pc55) as the template (plasmid pc55 described in Nophar et al., 1990) and the following primers:

```
Forward primer (SEQ ID NO: 7):
CATCATATGgatagtgtgtgtccccaagg
```

This primer has the Nde I restriction site (needed later for inserting the chimeric gene into the expression vector) followed by 20 nucleotides overlapping the 5' end of TBPI (the coding sequence is italicized).

```
Reverse primer (SEQ ID NO: 8):
AGGAAGCTTTattctcaatctggggtaggcac
```

This primer has 22 nucleotides overlapping the complementary 3' end of TBPI followed by nucleotides encoding the Hind III restriction site (needed later for ligating the DNA encoding TBPI to the DNA encoding PE).

The DNA encoding PE (FIG. 1E, SEQ ID NO: 3) which corresponds to nucleotides 1577-2659 of *Pseudomonas aeruginosa* exotoxin type A gene (accession number K01397, NCBI Gene Bank) was isolated by PCR 2 amplification (with High fidelity Taq polymerase from Boehringer Mannheim) using genomic DNA of serotype 61 of *Pseudomonas aeruginosa* (Leitner G. Kimron Veterinary Institute, Israel) as the template and the following primers:

```
Forward primer (SEQ ID NO: 9):
aattaaagcttccggaggtcccgagggcggcagcctggccgcgctgac
cgcg
```

Contained the HindIII restriction site (in italics), encoded a linker of six amino acids Ala-Ser-Gly-Gly-Pro-Glu and nucleotides 1577-1603 of the PE translocating domain (in bold).

```
Reverse primer (SEQ ID NO: 10):
aatgaattcttacttcaggtcctcgcgcggggg
```

Contained the EcoRI restriction site (in italics), a stop codon (tta) and nucleotides 2659-2679 of the PE ADP-ribosylation domain (in bold).

A PCR 2 product of 1058 bp was obtained.

In order to obtain the chimeric TBP-PE gene, the PCR 2 fragment comprising PE was ligated to the 3'-end of the PCR 1 fragment comprising TBPI via the HindIII restriction sites. The chimeric TBP-PE gene was inserted into the pETS-vector at the Nde I and EcoRI sites. The vector encoding the chimeric TBP-PE gene, referred herein pTBP-PE, was transformed and amplified in an *E. coli* strain (DH5α).

Example 2

Production of TBP-PE in Bacterial Cells

The bacterial strain BL21 (DE3) pLys, containing the TPB-PE vector (pTBP-PE) was cultured in 1 liter of Super broth with 0.4% glucose, 1.68 mM $MgSO_4$ and 100 μg/ml Ampicillin at 37° C. When absorbance at 600 nm reached 2.6, induction of recombinant protein expression was carried out by IPTG (isopropyl beta-D-thio-galactopyranoside) addition to the culture at a final concentration of 1 mM for about 90 minutes. Bacterial cells were harvested from the culture by centrifugation at 7500×g at 4° C. for 10 minutes and the cell pellet was kept frozen at −70° C. for 16 hours.

The frozen cell pellet was thawed on ice and re-suspended in 220 ml of buffer A [Phosphate buffered Saline without calcium and magnesium ("PBS w/o"), 50 mM EDTA, 5 mM $MgSO_4$, four tablets of complete protease cocktail (Roche), 30 mg/l DNaseI (Sigma)].

In order to breakdown cell clumps, the bacterial suspension was passed through an intradiscal 18G needle. Bacterial lysis and inclusion body isolation was carried out by either of the following methods:

Method I: first French Press 3×35 ml of cells at 5000 psi, and then twice at 15000 psi. Then lysed cells were centrifuged at 15,000 rpm at 4° C. 50 min (27,000×g) on a Sorval centrifuge, employing SS-34 rotor. The pellet was resuspended in 160 ml of "PBS w/o", containing 20 mM EDTA and 22 ml of 20% triton was added and incubated 5-10 minutes at room temperature. The inclusion bodies were precipitated by ultracentrifugation at 27,000×g at 4° C. for 50 min. The washes of the inclusion bodies with triton were repeated two more times, and were followed by three times washes with 160 ml PBS with 20 mM EDTA in the absence of triton.

Method II: 81 mg Lysozyme/20 ml PBS (20 ml of 405% solution of Lysozyme in PBS) was added to 110 ml of bacterial cells. The cells were stirred for 30 min at room temperature, transferred to ice and sonicated for 1 min 3 times. 16 ml of 20% triton (3% final concentration) were added, and inclusion bodies were isolated and washed as in method I.

The inclusion bodies, containing most of the recombinant protein (as judged by SDSPAGE and ADP rybosilase activity FIGS. 2 and 3 respectively), were dissolved in denaturation solution comprising 8M Urea, pH 12-12.8, containing 5 mM 2-mercaptoethanol. The volume of the denaturation solution used was equal to 443 times the inclusion body's wet weight. To promote full dissolution of the inclusion bodies they were vigorously vortexed and sonicated.

Protein was re-natured by dilution of about 10-20 times with 50 mM borate buffer at pH 9.5 and incubation of 18-20 hours at 4° C. with gentle stirring (200 rpm).

2.5 liters of refolded protein was concentrated 15 times by ultrafiltration trough ultrafilter PM30 (Amicon), and the final volume of the concentrated protein was about 170 ml. The concentration of refolded crude protein was estimated with the Bradford reagent to be about 70 μg/ml. TBP-PE chimeric protein was estimated to be about 60% of the refolded crude protein (from densitometry of protein band in SDS-PAGE). Therefore from 1 liter of bacterial culture about 7.65 mg of TBP-PE chimera were obtained, or from 500 mg inclusion bodies 3% of refolded crude protein was obtained of that 60% was the TBP-PE chimera.

Figure 2A:
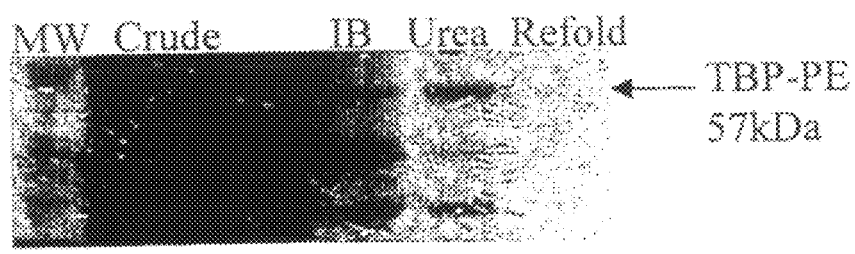
FIGS. 2 A-B show the chimeric protein TBP-PE expressed in bacterial *E. coli* cells resolved in SDS-PAGE. *E. coli* cells BL-21 pLys were transformed with pTBP-PE, an expression vector comprising pET-5 ligated to the TBP-PE chimeric gene. Following to transformation with pTBP-PE and to induction with isopropyl 13-D-thio-galactopyranoside (IPTG), *E. coli* transformants were lysed and the lysate ("crude") was fractionated into soluble proteins and insoluble inclusion bodies ("IB") as described in Example 2. Inclusion bodies were dissolved in 8M urea ("Urea") and refolded ("Refolded") as indicated in Example 2. Samples (20 μl per lane) of the crude, IB, urea and refolded fractions (FIG. 2 A) were resolved on SDS-PAGE (10%) and the gel was stained with a coomassie blue solution. The figure shows that chimeric TBP-PE protein, mainly found in the IB fraction, migrates on SDS-PAGE with an apparent molecular weight of approximately 57 kDa. MW-Molecular Weight standards. The refolded TBP-PE of Example 2 and FIG. 2 A was loaded in a Protein G-anti-TBP-I cross-linked affinity chromatography column. Column-bound TBP-PE was eluted by reducing the pH as indicated in Example 3. Eluted fractions were collected and the optical density at 280 nm (OD280) was measured. Samples (20 μl per lane) of the eluted fractions containing TBP-PE (lines 1-7 in FIG. 2B) and a purified non-chimeric TBP-I standard produced in Chinese hamster ovary (CHO) cells (line 8 in FIG. 2B) were loaded in SDS-PAGE (10%) and subjected to Western blot analysis detected with anti TBP-I. Although the MW predicted from the amino acid sequence of TBPI is 17 kDA, the apparent MW of TBPI was found to be higher, about 34 kDa (FIG. 2B line 8), due to glycosylation of this TBP-I standard produced in eukaryotic cells (CHO). Anti TBPI antibody detected also the chimeric TBP-PE of apparent molecular weight of about 57 kDa (FIG. 2B lines 1-7).

FIG. 2A shows that the refolded TBP-PE protein has the correct size of about 57 kDa predicted from the amino acid sequence.

Example 3

Affinity Purification of TBP-PE Chimera

The TBP-PE chimera was purified from the refolded crude extract comprising TBP-PE of Example 2 by affinity chromatography with an anti TBP-I cross-linked column.

For preparing the anti TBP-I cross-linked column, 2 mls. of protein G-Sepharose (or protein A for rabbit antibodies) (Amersham) were washed with 50 ml PBS (pH 7.5-8.0) for 3 times. 6 mg of monoclonal anti-TBPI antibody clone 20.11 (Engelmann et al. JBC 265 (24) 14497-504 1990) in 20 ml PBS, pH 7.5-8.0 (400 μA of stock 16.7 mg/ml) were added to the washed protein G-Sepharose, incubated at about 22° C. for 1.5 hours by shaking and washed twice with 10 volumes of 0.2M borate buffer (pH9.0 with NaOH). 100 μg crosslinker (DMP, PIERCE) (about 30-fold molar excess of crosslinker over the antibodies) in 4 ml borate buffer was added to the G-sepharose and antibody solution and incubated for 30 minutes. 20 ml of 50 mM Tris, pH 8.0 were added in order to stop the reaction and the solution was discarded. 20 ml of the same buffer were added for 15 minutes, the solution discarded and 20 ml of the same buffer added for 15 minutes on ice. The G-sepharose was washed with 100 mM NaCl in 100 mM citric acid, pH 3.5 followed by a wash with buffer at pH 2.0, to remove antibodies, which were not covalently bound to protein G.

A solution of 10 mM Tris, at pH 8.8 was used to restore the column for purification of the TBP-PE.

Figure 2B:
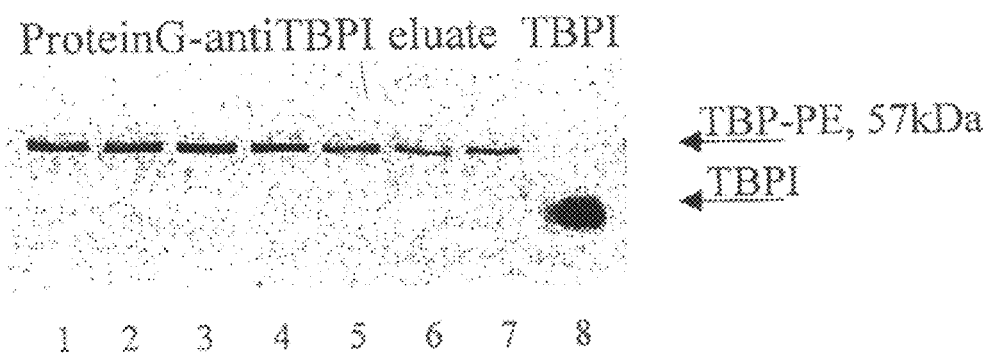

The refolded TBP-PE in borate buffer from Example 2 was loaded in the affinity chromatography column, and the column was washed with 10 column volumes of 10 mM Tris and 100 mM NaCl. The protein was eluted with 100 mM NaCl in 100 mM citric acid, pH 3.5. 0.5-1 ml fractions were collected and the optical density was measured at 280 nm. FIG. 2B shows a Western blot analysis of (20 ul μl) samples from the eluted fractions detected with anti TBPI monoclonal antibody. The results summarized in FIG. 2B show that although the MW predicted from the amino acid sequence of TBPI is 17 kDA, the apparent MW of TBPI was found to be higher, about 34 kDa (FIG. 2B line 8), due to glycosylation of this TBP-I standard produced in eukaryotic cells (CHO). It was demonstrated that the anti TBPI antibody recognize and bind the refolded TBP-PE protein to the affinity chromatography column and that the apparent molecular weight of TBP-PE is about 57 kDa (FIG. 2B lines 1-7).

Example 4

ADP-Rybosilation Activity of TBP-PE Protein In Vitro

In the preceding Example it was demonstrated that the refolded TBP-PE is recognized by TBPI antibodies. The following experiment was carried out in order to evaluate whether TBP-PE is capable of ADP-rybosylating elongation factor II (EF-2). The toxicity of Pseudomonas exotoxin is due to the capability of the exotoxin to block protein synthesis. The exotoxin inhibits incorporation of amino acids into protein immediately, provided the cofactor $NAD^+$ is present. In the presence of Pseudomonas exotoxin the adenosine diphosphate ribose moiety of $NAD^+$ is transferred into covalent linkage with elongation factor II (EF-2), producing an inactive derivative of the factor. The toxin acts catalytically in this reaction:

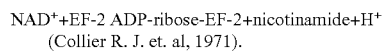
(Collier R. J. et. al, 1971).

In order to explore the ADP-ribosylating activity of the TBP-PE chimera, samples containing the refolded chimera or crude E. coli lysates before and after separation of the inclusion bodies, were incubated in a solution containing 200 μl of TE-50 (Tris, 50 mM, pH8) and 20 μl of EF-2 from wheat germ (Sigma). Then 10 μl of $NAD^{+-14}C$ was added the reaction mixture was vortexed shortly and incubated 20 min at 37° C. to allow incorporation of $NAD^+$-14C to EF-2 induced by TBP-PE. Following the 20 min. incubation, the proteins were precipitated by addition of 0.5 ml of 10% TCA (vortex), and centrifugation (5 min at 4° C., at 3000 rpm). After discarding the supernatant, the pellet was washed with 1 ml of 10% TCA, and 100 p. 1 of 1M NaOH were added for 10 minutes and mixed extensively (vortex) to allow dissociation of the pellet. After 10 minutes, 0.4 ml of 0.4M acetic acid was added and mixed. Incorporation of the radioactivity label into the protein was measured in 4 ml of scintillation solution in a gamma counter.

Figure 3:
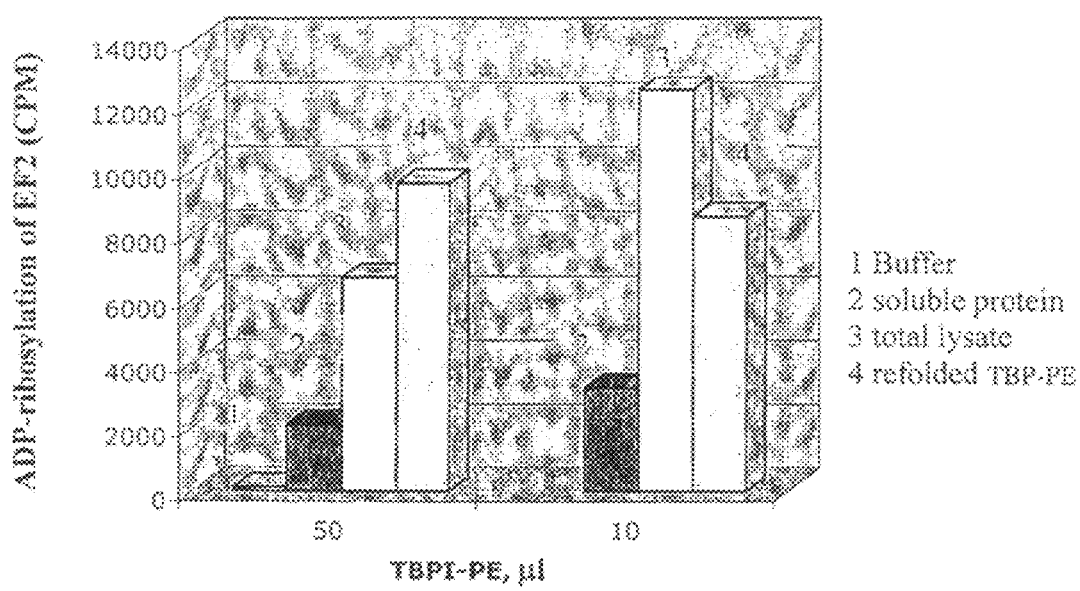
FIG. 3 shows ADP-rybosilation of elongation factor 2 (EF2) by TBP-PE. *Pseudomonas* exotoxin induces inhibition of protein synthesis mediated by ADP-rybosilation of EF2. To test the ADP-rybosylating activity of the chimeric protein TBP-PE, a sample of 10 and 50 μl of a cell lysate from transformed *E. coli* cells producing TBP-PE ("total lysate", bar 3), a cell lysate after separation of the inclusion bodies ("soluble protein", bar 2), refolded TBP-PE (from Example 2, bar 4), or of buffer (bar 1) was incubated in a solution comprising EF-2 and NAD$^+$-14C as indicated in Example 4. Incorporation of NAD$^+$-14C to EF-2 mediated by TBP-PE was measured as indicated in Example 4. The figure shows that TBP-PE induces ADP-ribosylation of EF2 (see bars 3 and 4 and compare to bar 1). A very low ADP-ribosylating activity was observed in the samples of soluble proteins (bar 2), indicating that most of the TBP-PE is present in the inclusion body fraction. A 10 μl sample of the total cell lysate fraction (which includes soluble protein and inclusion bodies) induced more activity than a 50 μl of the same fraction, suggesting the presence of some inhibitory activity in crude bacterial lysate. In contrast, it was observed that EF2 ADP-ribosylating activity increased with the amount of refolded TBP-PE added to the reaction (bar 4, compare activity of 10 and 50 μl).

As shown in FIG. 3, ADP-ribosylation of EF2 was induced by 10 μl of crude recombinant E. coli lysate (including soluble protein and inclusion bodies) protein and about half of the activity was observed using twice as much of the same crude lysate. A very low ADP-ribosylation activity could be observed in the soluble protein fraction (Supernatant obtained after French press). This result confirm that most of the chimeric protein is in the inclusion bodies.

The results obtained and summarized in FIG. 3 show that the refolded TBP-PE protein (from denatured inclusion bodies of Example 2) had EF2 ADP-ribosylating activity. The level of EF2 ADP-ribosylating activity of the refolded protein was comparable to that of the crude lysate (containing both the soluble proteins and the inclusion bodies). However, in contrast to the EF2 ADP-ribosylating activity of the crude lysate, the EF2 ADP-ribosylating activity of the refolded protein increased with the amount of refolded TBP-PE used in the reaction.

Example 5

Quantitation of Refolded TBP-PE by Enzyme-Linked Immunosorbent Assay (ELISA) and Binding Activity of Refolded TBP-PE to TNF The concentration of crude TBP-PE was first estimated with the Bradford reagent to be about 70 μg/ml (see Example 2) and then by densitometry analysis of the Western blot (FIG. 2A) to be of about 45 μg/ml.

The concentration of TBP-PE was measured by ELISA. For this purpose, PVC microtiter plates were coated with 50 μl monoclonal anti-TBPI antibodies (25 μg/ml in PBS) clone 20, (Engelmann et al. JBC 265 (24) 14497-504 1990). After incubation at 37° C. for 2 h the plate was washed three times with PBS and blocked for 2 hours at 37° C. with PBS containing 0.05% Tween20 and 1.5% BSA. Samples of TBPI (Prepared from recombinant CHO cells please confirm) or TBP1-PE were serially diluted in PBS containing 0.05% Tween20, 1% Hemoglobin, 0.65 M Sodium Chloride and 0.1% NP40. 50 μl of diluted sample was applied per well, in triplicates, incubated for 1 hour at 37° C. and washed five times with blotto (PBS containing 0.05% Tween20). Polyclonal rabbit anti-TBPI antibody diluted 1:1000 was applied in blotto for 1 hour at 37° C. or for over night at 4° C. and washed 5 times with the same solution. Secondary antibodies, anti-rabbit-HRP diluted 1:2000 were applied to the wells for 1 hour at 37° C. and the wells were washed five times with blotto. 100 μl of a fresh prepared ABTS solution (2,2'-azino-bis(3-ethylbenz-thiazoline-6-sulfonic acid, Sigma, cat A-1888), containing 0.01% $H_2O_2$ was added to the wells, incubated 30 minutes at 37° C. and the intensity of the green color developed was measured at 405 nm.

Figure 4A:
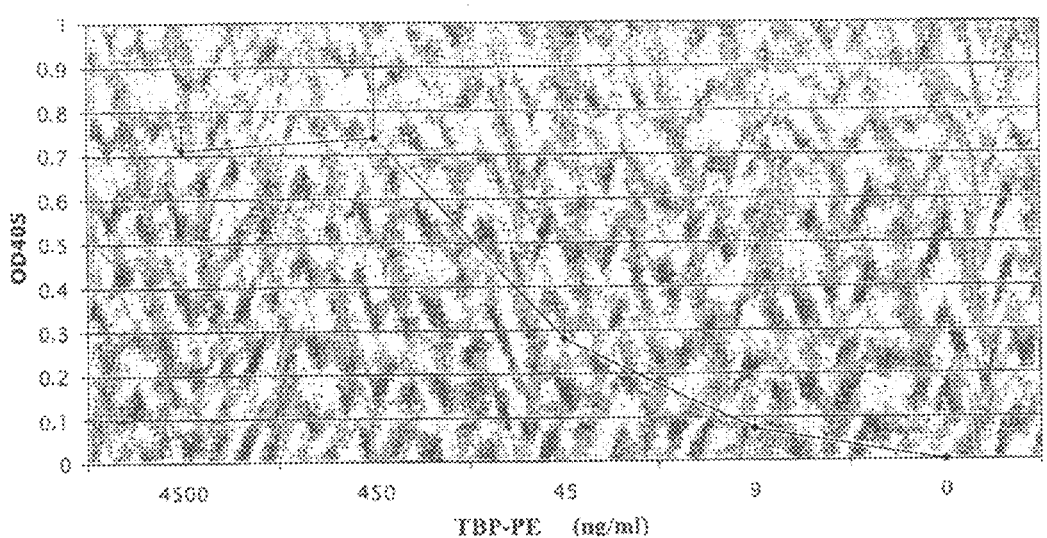
FIGS. 4 A-B show the quantitation of TBPI-PE (FIG. 4A) and TBPI (FIG. 4B) carried out by Enzyme-Linked Immunosorbent Assay (ELISA). To microtiter plates coated with monoclonal anti-TBPI, samples of serially diluted TBP1 (purified from CHO cells) or refolded TBP1-PE were applied in triplicates. After a 1-hour incubation of the plates at 37° C. followed by washes to remove non bound protein, bound TBP-PE or TBPI was detected using the polyclonal rabbit anti-TBPI, anti-rabbit-HRP conjugate and the HRP substrate as described in Example 5. The intensity of the green color, indicative of TBPI/TBP-PE concentration, was measured at 405 nm. According to the ELISA shown in FIG. 4B, O.D. of 0.3 is in the linear range and corresponds to a concentration of 76 μg/ml TBPI and the extrapolated concentration of the refolded TBPI-PE corresponds to about 45 μg/ml (FIG. 4A). The results summarized in FIG. 4 show that TBP-PE is correctly refolded and its concentration can be quantited by ELISA using anti TBP antibodies since anti-TBP antibodies recognize the refolded TBP-PE chimera as efficiently as they recognize the non-chimeric TBPI protein.
Figure 4B:
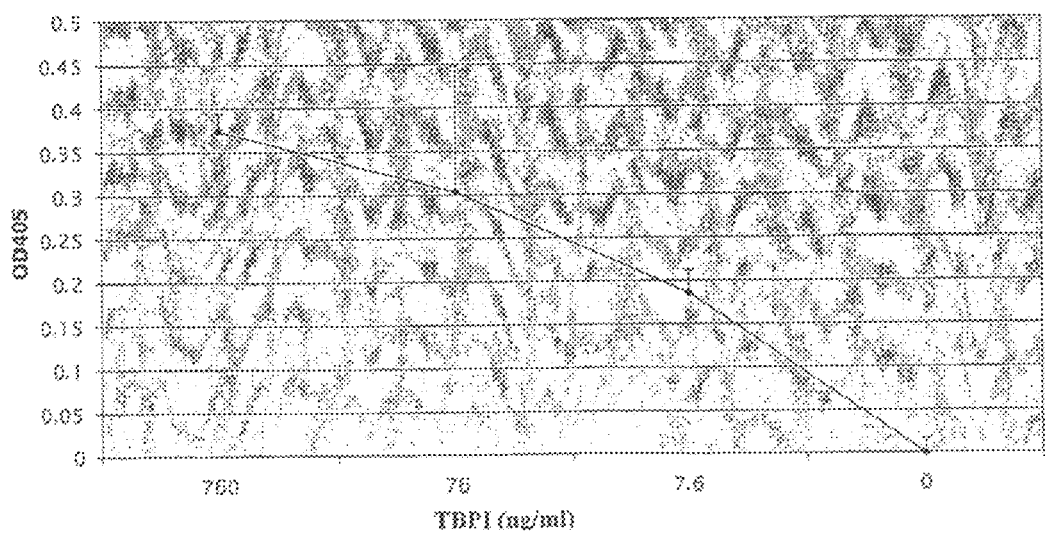

The results obtained and summarized in FIG. 4A show that the concentration of TBP-PE found by ELISA of 75 μg/ml was close to the concentration found by Bradford of about 45 μg/ml, and that the refolded TBP-PE and TBPI are recognized by anti-TBPI antibodies with similar efficiently.

In the following experiment, the binding of TBPI and TBPI-PE to TNF coated plates was compared. PVC 96-well microtiter plates were coated with TNF by incubation of the plates with a solution of 2 μg/ml pure human TNF-α (Beit-HaEmek) in 0.1M $Na_2CO_3$, pH9.6 containing 0.02% $NaN_3$, for 16 h at 4° C. The plates were then rinsed with PBS and incubated with 0.2 ml/well of PBS containing 3% BSA, 0.02% NaN3 (blocking solution) for 3 h at 37° C. 50 μl samples of refolded TBP-PE (45 μg/ml) or human TBPI (76 μg/ml) were applied per well in triplicates and the plates were incubated for 1 h at 37° C. When necessary, the samples were diluted in blocking solution. Following 1-hour incubation, the plates were washed three times with blocking solution. 50 μl of rabbit anti-TBPI antibodies, diluted 1:1000 in blocking solution were added to the wells, incubated for one hour at 37° C., or over night at 4° C. and washed three times with blocking solution. 50 μl of secondary antibody, anti-rabbit-HRP, at a 1:20,000 dilution were added to the wells, incubated for one hour at 37° C. and washed away three times with blocking solution. 100 μl of fresh prepared solution ABTS, containing 0.01% $H_2O_2$ was added and incubated 30 minutes at 37° C. The binding of the TBP-PE or TBPI to the plates was detected by the appearance of a green color, whose intensity was measured at 405 nm.

Figure 5A:
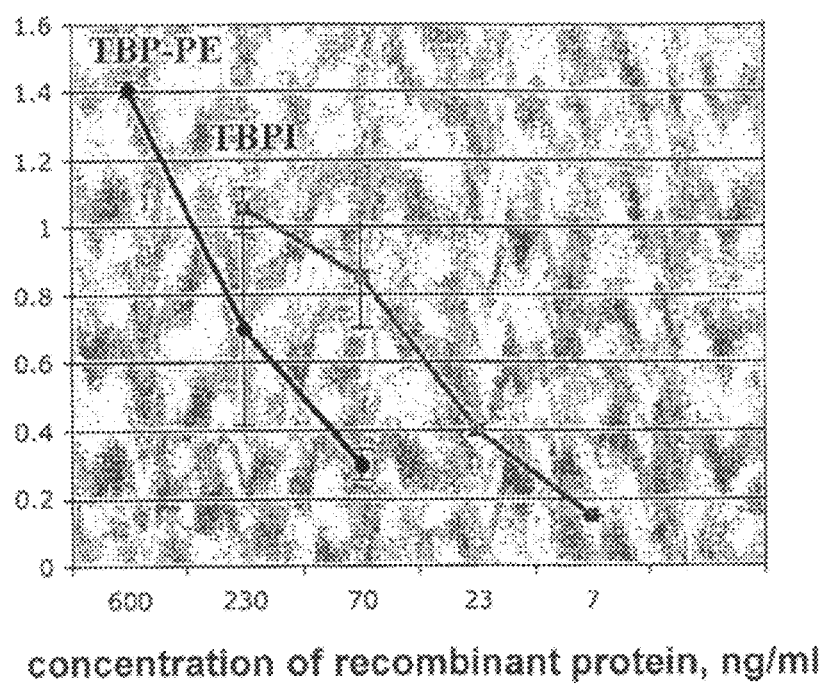
FIGS. 5 A-B show the TNF binding activity of TBP-PE vis-à-vis the TNF binding activity of TBP-1. The indicated amount of refolded TBP-PE or of non-chimeric HPLC-purified TBP-1 (produced in CHO cells) was loaded in TNF coated plates, and binding to the plates was detected with a monoclonal anti TBP-1 antibody. 5B shows the percentage of crude refolded chimeric protein having TNF binding activity. Using the activity of TBP-1 as 100% TNF binding, it was found that at least 50% of refolded TBP-PE had TNF binding activity.
Figure 5B:
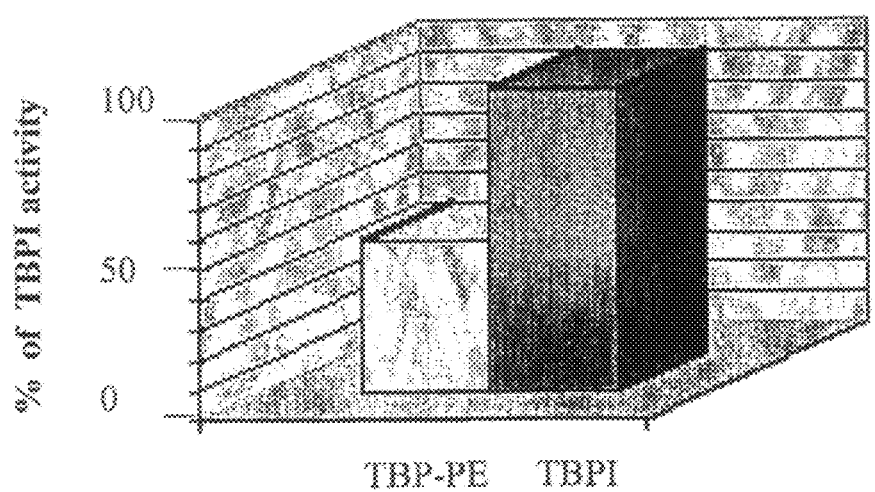

The results of the TNF-binding assay summarized in FIGS. 5 A-B show that 20 ng of crude refolded TBP-PE is nearly as active as 5 ng of TBPI (FIG. 5A). FIG. 5B shows the percentage of crude refolded chimeric protein having TNF binding activity. Using the activity of TBPI as 100% TNF binding, it was found that at least 50% of refolded TBP-PE had TNF binding activity.

Example 6

Cells Lines Overexpressing TNF on their Surface

Two cell lines were used for exploring the cytotoxic effect of TBP-PE: (a) the human acute monocytic leukemia THPI cells (obtained from the German Collection of Microorganisms and Cell Culture). Monocytic differentiation of these cells can be induced with phorbol myristate acetate (PMA). These cells are cultured at a cell density range of 0.3–1×10$^6$/ml in RPMI 1640 medium supplemented with 10% Fcs, 2 mM L-glutamine, 1 mM Na-pyruvate, 1% nonessential amino acids, 9 mg/ml Insulin, 100 mg/ml penicillin and 100 mg/ml streptomycin. To enhance cell surface TNF expression, these cells, activated with PMA (for 16-20 hours, 100 ng/ml) were treated with LPS (1 mkg/ml for 1.5 h) and with 10 μg/ml metalloprotease inhibitor GM6001 (Calbiochem) for two hours prior to tests.

b) HeLa-M9 cells, a clone of the epithelial HeLa cervical carcinoma line that constitutively expresses under control of the SV40 promoter a human TNF mutant cDNA in which the arginine at position +2 and the serine at position +3 are substituted for threonines. These mutations cause an about tenfold reduction in the cleavage rate of 26 kDa TNF. The cells are cultured in RPMI 1640 medium supplemented with 10% Fcs, 2 mM L-glutamine, 100 mg/ml penicillin, 100 mg/ml streptomycin and 50 mg/ml gentamycin.

TNF-expression on the cell surface of THPI cells was assessed by FACS in presence of inhibitor of metalloproteases GM6001, 10 mg/ml (Calbiochem) to prevent shedding of TNF-α. Samples of 5×10$^5$ cells were incubated in Fcs-free RPMI, containing Insulin, 1 mkg/ml, Transferrin, 1 mg/ml, Na Selenite, 1 ng/ml, Na Pyruvate, non-essential amino acids, glutamine with PMA 50-100 ng/ml for 16 h. Then LPS E. coli 0111-B4 was added at concentration 1 mg/ml together with GM6001, 10 mg/ml for 2 h. For FACS analysis of TNF-expression on cell surface, cells were washed at 4 C in phosphate buffered saline (PBS) containing 2 mg/ml BSA, 0.1% sodium azide and incubated with FITC-anti-humanTNF antibodies. Analysis was performed by FACScan (Becton. Dickinson, Mountain View, Calif.). It was found that at least 30% of cells express TNF-α on their surface.

Example 7

Cytotoxicity of TBP-PE

The cytotoxic activity of the chimeric protein TBP-PE (and as control the soluble TNF receptor alone) was tested with two types of cells, epithelial cells and monocytic-like cells, both overexpressing membrane bound TNF.

HeLa-M9 cells is a clone of the epithelial HeLa cervical carcinoma line that constitutively expresses under the control of the SV40 promoter a human TNF mutant cDNA in which the arginine at position +2 and the serine at position +3 are substituted for threonines. These mutations cause about tenfold reduction in the cleavage rate of 26 kDa surface TNF. The cells are cultured in RPMI 1640 medium supplemented with 10% Fcs, 2 mM L-glutamine, 100 mg/ml penicillin, 100 mg/ml streptomycin and 50 mg/ml gentamycin.

The HeLa-M9, or HeLa were seeded in 96-well plates at density 4×10$^4$ cells per well. Different concentrations of TBP-PE or TBPI were added to the wells for 3 hours. To some wells TBPI was applied simultaneously with TBPI-PE to compete for TNF in order to check specificity of TBP-PE action through membrane TNF-α. After the 3-hour incubation, the medium was replaced with medium alone without the recombinant proteins, and the cells were allowed to grow for 24 hours and viability of the cultures was assessed using Neutral Red.

The results obtained are summarized in FIG. 6A and show that 600 ng/ml of TBP-PE were not cytotoxic to HeLa cells but caused death of at of HeLa-M9 cells overexpressing TNF-α on their surface. TBPI specifically blocked the cytotoxic effect of TBP-PE, when applied in 10-fold excess. TBPI alone did not cause cytopathic effect at concentrations of up to 76 μg/ml. Two different batches of TBP-PE were tested and were found to be similarly cytotoxic. The results shown on FIG. 6A, show that TBP-PE caused more than 90% cell death in HeLaM9 cells at concentrations of 600 ng/ml. One of the batches of TBP-PE was very active and was cytotoxic at concentrations as low as 0.06 mg/ml, killing nearly 65% of HeLaM9 cells.

In order to explore cytotoxicity of the chimeric TBP-PE on an activated monocytic-like cell line, THP1 (see Example 6) were seeded at density 200,000 cells per well in 96-well plate in fetal calf serum (Fcs)-free RPMI, containing insulin, 1 mkg/ml, transferrin, 1 mg/ml, Na selenite, 1 ng/ml, Na pyruvate, non-essential amino acids, glutamine with PMA 50-100 ng/ml for 16 h (to induce monocytic-like phenotype and exposure of the LPS receptor). Then E. coli LPS (0111-B4) was added at a concentration 1 mg/ml (to induce TNF expression) together with GM6001 (a metalloproteinase inhibitor to prevent TNF shading from the cell surface) at a concentration of 10 mg/ml for 1-1.5 hours. The resulting PMA-LPS-GM6001-treated THP1 cells show a phenotype characteristic of monocytic cells having a large amount of surface TNF. These monocytic-like cell lines were incubated with 60 and 600 ng/ml of refolded TBP-PE for about 20 hours and stained with neutral red for estimating survival. When indicated, recombinant human TBP-1 was added immediately before the refolded chimeric protein to compete for binding to the cell surface TNF.

As shown in the results summarized in FIG. 6B, it was found that TBP-PE, used at concentrations causing cytotoxicity of HeLaM9 cells (60 and 600 ng/ml), did not cause cell death of activated THP1.

The activity of refolded TBP-PE was tested also in LPS-activated primary macrophages. For the preparation of primary macrophages, female mice C57BL/6 was injected intraperitoneally (i.p.) with 1.5 ml sterile Brewer's thioglycolate broth (Difco) for 4 days. The peritoneal exudates (>85% macrophages) was harvested at day 4, washed with PBS by centrifugation and seeded in 96-well flat bottom plates at 1×100,000 macrophages/well in RPMI with 10% heat inactivated Fcs. The cells were allowed to adhere for 18 h. Non-adherent cells were removed by washing with warm medium.

For inducing macrophage activation, a macrophage monolayer was treated with the LPS (E. coli LPS 011:B4) at concentrations indicated in FIG. 6C (1 μg/ml and 10 μg/ml) for 1 h in presence of 5 mg/ml GM6001 (Calbiochem). After LPS treatment, the cells were incubated for two more hours in the presence or in the absence of 6000 and 15000 ng/ml refolded TBP-PE. Next, the medium was replaced for RPMI+10% heat inactivated fetal calf serum (HFcs) with the same concentration of LPS, but without GM6001 to allow for secretion of TNF-α into the cell culture medium. The cell culture medium of over night-incubated macrophages was collected and the TNF-α, in the medium was measured by a bioassay (see below and FIG. 6D).

The results obtained, summarized in FIG. 6C, show that TBP-PE was not cytotoxic for activated primary macrophages.

The levels of TNF secreted in the growth medium of LPS-activated primary macrophages treated with TBP-PE or untreated were assessed (FIG. 6D). Medium of activated primary macrophages was collected, diluted two, four and eight folds (0.5, 0.25, 0.125 respectively) with fresh medium and applied to a monolayer of TNF sensitive cells (L929) seeded at density 1×10$^5$ cells per well (on 96-well plates). The bioassay was carried out in the presence of 10 mg/ml cycloheximide. L929 cells (murine connective tissue clone L929 ATCC Number CCL-1) were incubated with the conditioned medium of activated macrophages and incubated for 20 hours. The level of L929 cytotoxicity was proportional to the concentration of TNF present in the conditioned medium.

As shown on FIG. 6D, macrophages from thioglycolate-treated mice produced some TNF-α. For example, two or four fold diluted medium of the thioglycolate treated peritoneal macrophages caused death of more than 40% TNF-sensitive L929 cells. However, additional macrophage activation by LPS augmented TNF secretion. For example, L929 cell death was higher than 60% when the cells were exposed to highly (eight fold) dilute conditioned medium of LPS activated macrophages (FIG. 6D). Conditioned medium of activated primary macrophages treated with TBP-PE was found to be equally toxic for L929 as conditioned medium of activated macrophages without the TBP-PE treatment (FIG. 6D). This result indicates that TBP-PE does not inhibit TNF secretion in primary activated macrophages.

These results show that TBP-PE does not cause death of activated primary macrophages and does not inhibit TNF secretion in LPS activated primary macrophages.

In all, the results obtained show that TBP-PE has the following specific effect, which can be exploited for therapeutical purposes: it specifically kills epithelial cells overexpressing TNF.

Example 8

Inhibition of Protein Synthesis in HeLa M9 Cells Mediated by TBP-PE

HeLa-M9 and HeLa cells were seeded one day before the assay in 96-well tissue culture plates at a density of 4×10$^4$ cells per well. TBP-PE at a concentration of 600 ng/ml was added to the cells for 3 hours. In some of the wells TBPI was applied simultaneously with TBPI-PE to compete for TNF binding. After the 3-hour incubation, the medium was replaced with DMEM+10% Fcs, and the cells were allowed to grow for 16 additional hours. The cells were washed once with PBS, incubated for 10 minutes in Met, Cis-free RPMI, and for 30 minutes with 100 ml of $^{35}$S-Met-containing Met, Cis-free RPMI (55 mcCi/100 μl of $^{35}$S-Met). After the 30 min incubation, the medium was removed, the cells were washed three times with Met, Cis-free RPMI, Lysed in 200 μl SDS-buffer [1%SDS in PBS, 20 mM 2-mercaptoethanol, 2 mM EDTA] and preheated to 100° C. The cell lysates were transferred to microtubes, boiled for 5 min., and centrifuged for 5 min. The protein in the supernatant (about 100 μl volume) was subjected to TCA precipitation.

For TCA precipitation, 0.5 ml 10% of ice-cold TCA and 20 μl of 3% BSA were added to the sample containing the supernatant. The sample was allowed to precipitate on ice for 15 minutes and was centrifuged for 5 min at 4° C., at 3000 rpm. The TCA precipitate was washed with 1 ml TCA and 100 μl of 1M NaOH incubated for 10 min and vortexed. To allow the pellet to completely dissolve, 0.4 ml of 0.4M of acetic acid were added to the solution and mixed thoroughly. Radioactivity was measured in 4 ml scintillation solution and monitored in a beta-counter.

As shown on FIG. 7, as few as 600 ng/ml of TBP-PE inhibited about 70% protein synthesis in HeLa-M9 cells, but in contrast, the same amount of TBP-PE did not impair the synthesis of proteins in HeLa cells. TBPI was found to inhibit the inhibitory effect of TBP-PE in protein synthesis when TBPI was added together with TBP-PE at 10-fold excess. TBPI alone did not affect the synthesis of proteins neither in HeLa-M9, nor in HeLa cells.

Example 9

Internalization Assay

TNF-α expressing cells (HeLa M9 or others) are labeled with [$^{125}$I]-conjugate (1 μg/ml) at 37° C. in medium containing 0.1 mg/ml of BSA. The cells are then trypsinized and washed with ice-cold PBS, resuspended in 0.3% Pronase in PBS and left for 40 min at 2 C before centrifugation through dibutylphthalate. Endocytosis efficiency is expressed as the pronase-resistant percentage of cell-associated [$^{125}$I]-conjugate after 30 min of uptake (modified from Taupiac M-P. et. Al, 1999).

Example 10

SDS-PAGE and Immunoblotting

Cells pellets collected by centrifugation were dissolved in Laemmli buffer. Samples were boiled for 5 minutes prior to application to a 0.1% SDS, 10% acrylamide slab gel. The gels can be stained by comassie blue or by silver staining.

For immunoblotting, samples after electrophoresis were transferred to a nitrocellulose paper, followed by reaction with antibody to the toxin or to the soluble form of the TNF receptor, then a second antibody linked to HRP (for the toxin-goat anti-rabbit antibody, for the soluble TNF receptor—goat anti mouse antibody) was applied and staining was carried out with the HRP substrate. The monoclonal antibodies against the soluble TNF receptors are as described [1,5] [16].

Example 11

Animal Toxicity

Six month old Blab/c mice are injected intraperitoneally with varying doses of the chimeric protein (and, as controls, of the toxin and of the soluble TNF receptor incorporated to the chimeric protein) at the range of 0.1 μg/mouse to 40 μg/mouse. Viability of the mice is assessed after 48 h and later.

Example 12

Activity of the Chimeric Protein Against Tumor Cells Expressing TNF on their Surface In Vivo The in vivo cell killing activity of the chimeric protein (and, as controls, of the toxin and of the soluble TNF receptor incorporated to the chimeric protein) is assessed in mice bearing a tumor that produces cell-bound TNF. Confluent cultures of HeLa-M9 cells are harvested with 5 mM EDTA in PBS and suspended followed by washing twice with PBS. Balb/c nude mice (aged 7-8 weeks and weighing 20-21 g) are inoculated subcutaneously in the flank area with the HeLa-M9 cells ($1\times10^7$ cells/0.1 ml/mouse). Five days later the mice are injected intraperitoneally with various doses of the tested chimeric protein and then injected again once weekly. The occurrence, size and weight of tumor at the site of inoculation of the cells are assessed 11 weeks later.

Example 13

Therapeutic Activity of the Chimeric Protein in a Murine Model for Spontaneous Development of Arthritis Transgenic mice expressing a human TNF transgene in which the 3' noncoding region, which provides translational regulation of its expression was expressed with that of the β-globin gene [17] are used. Two weeks after birth, the mice are injected intraperitoneally with various doses of the tested chimeric protein (the following are used to inject mice as controls: the toxin alone or the soluble TNF receptor alone) and then injected again once weekly for a period of 9 weeks. Swelling of the hind leg ankle joints of the mice are assessed periodically by determining the diameter of the joint. Lesions/alterations involving the joint structures: joint capsule, joint space, synovial membrane, articular cartilage, and subchondral bone are evaluated histologically.

Example 14

Therapeutic Activity of the Chimeric Protein in a Murine Model for Antigen-Induced Arthritis Lewis rats are immunized in the hind flank with 0.5 mg methylated bovine serum albumin (mBSA) in complete Freund's adjuvant. Twenty-one days later (day 0), the animals are injected in both hind knee joints with 50 μg mBSA in pyrogen-free saline. The rats are injected intra-articularly with the tested protein (as controls, the toxin alone or the soluble TNF receptor alone are injected) in both knee joints on that day and on the following 2 days (days 0, 1 and 2). Knee joint width is measured daily on days 0-6 relative to treatment. Histopathological examination of the joints harvested on day 6 is performed. Lesions/alterations involving the knee joint structures: joint capsule, joint space, synovial membrane, articular cartilage, and subchondral bone are evaluated.

Example 15

Therapeutic Activity of the Chimeric Protein in a Murine Model for Antigen-Induced Arthritis Male DBA/1 mice (8-12 weeks old) are immunized with 100 μg of type II collagen emulsified in FCA (Difco, Detroit, Mich.) by intradermal injection at the base of the tail. Starting from the time of immunization, the mice are injected intraperitoneally twice weekly with the test protein (as controls, the toxin alone or the soluble TNF receptor alone are injected) in PBS until onset of clinical arthritis. From day 15 after immunization mice are examined daily, for 10 days, for onset of disease using two clinical parameters: paw swelling and clinical score. Paw swelling is assessed by measuring the thickness of the first affected hind paw with callipers.

Example 16

Therapeutic Activity of the Chimeric Protein in a Murine Model for of Colitis

IL-10 knockout mice, purchased in Harlan UK are interbred to generate mice homozygous for IL10 gene deletion and screened for homozygocity by PCR done on their tail DNA. Starting at the age of 4 weeks, the mice are injected intraperitoneally three times weekly with the test protein (as controls, the toxin alone or the soluble TNF receptor alone are injected) in PBS till the age of 20 weeks. The clinical score, histological analysis of the intestine and the content of inflammatory cytokines in the stools were evaluated as described in [18].

Example 17

Construction of a Plasmid for the Expression of a Conjugate of the Soluble Form of the P75 TNF Receptor The sequence of the soluble form of the p75 TNF receptor (TNFRSF1B, Genbank ID M32315) incorporated into the conjugate corresponds to the full sequence of the extracellular domain of the receptor (Leu 1 till Asp 235). This sequence is fused to that of PE and inserted into the pET-vector as described for example 1.

REFERENCES

1. Beutler, B. A., *The role of tumor necrosis factor in health and disease.* J Rheumatol, 1999. 26 Suppl 57: p. 16-21.
2. Kollias, G., et al., *On the role of tumor necrosis factor and receptors in models of multiorgan failure, rheumatoid arthritis, multiple sclerosis and inflammatory bowel disease.* Immunol Rev, 1999. 169: p. 175-94.
3. Reimold, A. M., *New indications for treatment of chronic inflammation by TNF-alpha blockade.* Am J Med Sci, 2003. 325(2): p. 75-92.
4. Andreakos, E. T., et al., *Cytokines and anti-cytokine biologicals in autoimmunity: present and future.* Cytokine Growth Factor Rev, 2002. 13(4-5): p. 299-313.
5. Wallach, D., et al., *Tumor necrosis factor receptor and Fas signaling mechanisms.* Annu Rev Immunol, 1999. 17: p. 331-67.
6. Locksley, R. M., N. Killeen, and M. J. Lenardo, *The TNF and TNF receptor superfamilies: integrating mammalian biology.* Cell, 2001. 104(4): p. 487-501.
7. Jankovic, D., Z. Liu, and W. C. Gause, *Th1-and Th2-cell commitment during infectious disease: asymmetry in divergent pathways.* Trends Immunol, 2001. 22(8): p. 450-7.
8. Lugering, A., et al., *Infliximab induces apoptosis in monocytes from patients with chronic active Crohn's disease by using a caspase-dependent pathway.* Gastroenterology, 2001. 121(5): p. 1145-57.
9. van Deventer, S. J., *Transmembrane TNF-alpha, induction of apoptosis, and the efficacy of TNF-targeting therapies in Crohn's disease.* Gastroenterology, 2001. 121(5): p. 1242-6.
10. Van den Brande, J. M., et al., *Infliximab but not etanercept induces apoptosis in lamina propria T-lymphocytes from patients with Crohn's disease.* Gastroenterology, 2003. 124(7): p. 1774-85.
11. Brinkmann, U. and I. Pastan, *Recombinant Immunotoxins: From Basic Research to Cancer Therapy.* Methods, 1995. 8: p. 143-156.
12. Pastan, I. I. and R. J. Kreitman, *Immunotoxins for targeted cancer therapy.* Adv Drug Deliv Rev, 1998. 31(1-2): p. 53-88.
13. Pastan, I., *Immunotoxins containing Pseudomonas exotoxin A: a short history.* Cancer Immunol Immunother, 2003. 52(5): p. 338-41.
14. Ben-Yehudah, A., et al., *Utilizing chimeric proteins for exploring the cellular fate of endogenous proteins.* Biochem Biophys Res Commun, 2002. 290(1): p. 332-8.
15. Engelmann, H., et al., *Antibodies to a soluble form of a tumor necrosis factor (TNF) receptor have TNF-like activity.* J Biol Chem, 1990. 265(24): p. 14497-504.
16. Bigda, J., et al., *Dual role of the p75 tumor necrosis factor (TNF) receptor in TNF cytotoxicity.* J Exp Med, 1994. 180(2): p. 445-60.
17. Keffer, J., et al., *Transgenic mice expressing human tumour necrosis factor: a predictive genetic model of arthritis.* Embo J, 1991. 10(13): p. 4025-31.
18. Scheinin, T., et al., *Validation of the interleukin-10 knock-out mouse model of colitis: antitumour necrosis factor-antibodies suppress the progression of colitis.* Clin Exp Immunol, 2003. 133(1): p. 38-43.

The invention claimed is:

1. A chimeric protein comprising the amino acid sequence of at least one polypeptide consisting of an extracellular portion of a TNF receptor, said polypeptide being connected to a *Pseudomonas* exotoxin fragment, wherein the *Pseudomonas* exotoxin fragment lacks the cell binding domain and wherein said extracellular portion of the TNF receptor binds TNFα.

2. The chimeric protein according to claim 1, wherein the protein comprises *Pseudomonas* exotoxin domains II, Ib and III.

3. The chimeric protein according to claim 2, wherein said fragment of *Pseudomonas* exotoxin (PE) comprises the amino acid sequence of SEQ ID NO: 4.

4. The chimeric protein according to claim 1, comprising the amino acid sequence of SEQ ID NO: 2.

5. An isolated DNA sequence encoding a chimeric protein comprising the amino acid sequence of at least one polypeptide consisting of an extracellular portion of a TNF receptor, said polypeptide being connected to a *Pseudomonas* exotoxin fragment, wherein the *Pseudomonas* exotoxin fragment lacks the cell binding domain and wherein said extracellular portion of the TNF receptor binds TNFα.

6. The DNA sequence according to claim 5, further encoding a signal peptide for secretion in eukaryotic cells.

7. The DNA according to claim 5, comprising the nucleotide sequence of SEQ ID NO: 1.

8. An expression vector comprising a DNA sequence according to claim 5.

9. A host cell comprising an expression vector according to claim 8.

10. The host cell according to claim 9, wherein the cell is an eukaryotic cell.

11. The host cell according to claim 10, wherein the eukaryotic cell is selected from the group consisting of HeLa, CHO, HEK293, THPI, Yeast, and insect cells.

12. The host cell according to claim 9, wherein the cell is a prokaryotic cell.

13. A method for producing a chimeric protein, comprising culturing a host cell according to any one of claims 9 to 12 and isolating the chimeric protein produced.

14. A pharmaceutical composition comprising a chimeric protein according to claim 1 and a pharmaceutically acceptable carrier.

15. The pharmaceutical composition according to claim 14, wherein the chimeric protein is TBP-PE.

16. A composition comprising a DNA according to claim 5 and a carrier.

17. A composition comprising a vector according to claim 8 and a carrier.

* * * * *